US007314860B2

(12) United States Patent
Lassila et al.

(10) Patent No.: US 7,314,860 B2
(45) Date of Patent: Jan. 1, 2008

(54) HEPARIN-LIKE COMPOUNDS, THEIR PREPARATION AND USE TO PREVENT ARTERIAL THROMBOSIS ASSOCIATED WITH VASCULAR INJURY AND INTERVENTIONS

(75) Inventors: Riitta Lassila, Espoo (FI); Petri Kovanen, Espoo (FI); Ken Lindstedt, Helsinki (FI)

(73) Assignee: Jenny Ja Antti Wilhurin Rahasto, Helsinki (FI)

( * ) Notice: Subject to any disclaimer, the term of this patent is extended or adjusted under 35 U.S.C. 154(b) by 476 days.

(21) Appl. No.: 10/418,095

(22) Filed: Apr. 18, 2003

(65) Prior Publication Data

US 2003/0212042 A1 Nov. 13, 2003

Related U.S. Application Data

(62) Division of application No. 09/230,097, filed as application No. PCT/FI98/00925 on Nov. 25, 1998, now abandoned.

(30) Foreign Application Priority Data

Nov. 25, 1997 (FI) ..................................... 974321

(51) Int. Cl.
  *A61K 38/39* (2006.01)
  *A61F 2/06* (2006.01)
(52) U.S. Cl. ............................... 514/8; 514/54; 514/63; 623/1.43
(58) Field of Classification Search .................... 514/8, 514/54, 63; 623/1.43
  See application file for complete search history.

(56) References Cited

U.S. PATENT DOCUMENTS

| 4,265,927 | A |   | 5/1981  | Ericksson et al.       |
|-----------|---|---|---------|------------------------|
| 4,350,629 | A |   | 9/1982  | Yannas et al.          |
| 4,863,907 | A |   | 9/1989  | Sakurai                |
| 5,019,393 | A | * | 5/1991  | Ito et al. ...... 424/423 |
| 5,041,292 | A |   | 8/1991  | Feijen                 |
| 5,071,973 | A |   | 12/1991 | Keller et al.          |
| 5,162,430 | A |   | 11/1992 | Rhee et al.            |
| 5,510,418 | A |   | 4/1996  | Rhee et al.            |
| 5,529,986 | A |   | 6/1996  | Larsson et al.         |
| 5,571,166 | A |   | 11/1996 | Dinh et al.            |
| 5,618,298 | A |   | 4/1997  | Simon                  |
| 5,643,580 | A |   | 7/1997  | Subramaniam            |
| 5,702,754 | A |   | 12/1997 | Zhong                  |
| 5,851,230 | A |   | 12/1998 | Weadock et al.         |
| 5,869,127 | A |   | 2/1999  | Zhong                  |
| 5,876,433 | A | * | 3/1999  | Lunn ............ 623/1.15 |

FOREIGN PATENT DOCUMENTS

| EP | 0 341 006    | 11/1989 |
| EP | 0 454 599 A1 | 10/1991 |
| WO | 89/05646     | 6/1989  |
| WO | 91/15252     | 10/1991 |
| WO | 93/05074     | 3/1993  |
| WO | 93/06836     | 4/1993  |
| WO | 97/19701     | 6/1997  |

OTHER PUBLICATIONS

Schurmann, K. et al "Iliac arteries: plain and heparin-coated . . . " Radiology (1997) vol. 203, pp. 55-60.*
Fram, D. et al "Local delivery of heparin to balloon angoiplasty sites . . . " Cath. Cardiovasc. Diag. (1997) vol. 41, pp. 275-286.*
Suzuki, S. et al "Glycosaminoglycan chains of preoteoglycans . . . " Pure Appl. Chem. (1991) vol. 63, No. 4, pp. 545-554.*
Serruys, P. et al "Heparing-coated Palmaz-Schatz stents in human coronary arteries . . . " Circulation (1996) vol. 93, No. 3, pp. 412-422.*
Lindstedt et al., "Soluble Heparin Proteoglycans . . . ", J. Lipid Res., 1992, pp. 65-75, vol. 33, Stanford University Libraries' HighWire Press, Stanford, California, USA.
Messmore et al., "In Vitro Studies of the Interaction of Heparin, Low Molecular Weight Heparin and Heparinoids with Platelete", from Heparin and Related Polysaccharides—Structures and Activities, ed. OFOSU, p. 21, NY Acad of Sci, New York, New York, USA.
Mattsson et al , "Antithrombotic Effects of Heparin Oligosaccharides", from Heparin and Related Polysaccharides—Structures and Activities, ed. OFOSU, pp. 323-332, NY Acad of Sci, New York, New York, USA.
Hardhammer et al., "Reduction in Thrombotic Events with Heparin-Coated Palmaz-Schatz Stents in Normal Porcine Coronary Stents", Circulation, 1996, pp. 423-430, vol. 93, No. 3, Stanford University Libraries' HighWire Press, Stanford, California, USA.

(Continued)

*Primary Examiner*—Leigh C. Maier
(74) *Attorney, Agent, or Firm*—Buchanan Ingersoll & Rooney, PC

(57) ABSTRACT

The present invention is related to heparin-like compounds characterized by their capacity of inhibiting collagen-induced platelet aggregation in flowing whole blood and their use for prophylactic treatment of arterial thrombosis associated with vascular or microvascular injury and interventions. Said properties are related to a high coupling density of negatively charged heparin or heparin-like glycosaminoglycan molecules, present in multiple heparin or heparin-like glycosaminoglycans as well as in proteoglycans containing said multiple heparin or heparin-like glycosaminoglycans or lower-molecular-weight heparin or heparin-like glycosaminoglycans connected directly or through spacer/linker molecules to globular core molecules. Heparin-like compounds, with said properties are obtainable from mammalian mast cells, by tissue extraction or cell cultivation. The heparin-like compounds of the present invention can also be produced by synthetical, semisynthetical and/or biotechnological methods and they are useful for manufacturing preparations, means and devices for local or topical application in prophylactic treatment of arterial thrombosis and its sequelae.

3 Claims, 10 Drawing Sheets

OTHER PUBLICATIONS

De Scheerder et al., "Experimental Study of Thrombogenicity and Foreign Body Reaction Induced by Heparin-Coated Coronary Stents", Circulation, 1997, pp. 1549-1553, vol. 95, No. 6, Stanford University Libraries' HighWire Press, Stanford, California, USA.

Nader, "Characterization of a Heparin Sulfate and a Peculiar Chrondroitin 4-Sulfate Proteoglycan from Platelets", The Journal of Biological Chemistry, 1991, pp. 10518-10523, vol. 266, No. 16, American Society for Biochemistry and Molecular Biology, Bethesda, Maryland, USA.

Sobel et al., "Heparin Inhibition of vonWillebrand Factor-Dependent Platelet-Function In Vitro and In Vivo", Journal of Clinical Investigation, 1991, pp. 1787-1793, vol. 87, No. 5, Stanford University Libraries' HighWire Press, Stanford, California, USA.

Lassila et al., "Native Macromolecular Heparin Proteoglycans Exocytosed from Stimulated Rat Sterosal Mast Cells Strongly Inhibit Platelet-Collagen Interactions", Arteriosclerosis Thrombosis and Vascular Biology, 1997, pp. 3578-3587, vol. 17, No. 12, Stanford University Libraries' HighWire Press, Stanford, California, USA.

Riitta Lassila, et al., "Native Macromolecular Heparin Proteoglycans Exocytosed From Stimulated Rat Serosal Mast Cells Strongly Inhibit Platelet-Collagen Interactions", Arteriosclerosis, Thrombasis, and Vascular Biology, pp. 19-28, vol. 17, No. 12, Dec. 1997.

"Dorland's Illustrated", 27$^{th}$ Edition Medical Dictionary, p. 1165, W.B. Saunders Company, Harcourt Brace Jovanovich, Inc.

Rothenberg et al., "Influence of the Fibroblast Environment on the Structure of Mast Cell Proteoglycans" in Heparin and Related Polysaccharides, ed. OFOSU, 1989, pp. 233-244.

Schurmann et al., "Iliac Arteries: Plain and Heparin-Coated Dacron-Covered Stent-Grafts Compared with Noncovered Metal Stents—An Experimental Study", Radiology, 1997, pp. 55-63, vol. 203, No. 1, Stanford University Libraries' HighWire Press, Stanford, California, USA.

Ritter et al., "Heparin Coating of Vascular Prostheses Reduces Thromboemboli", Surgery, 1997, pp. 888-892, vol. 122, No. 5, Elsevier Science, London, England.

The Merck Index (12$^{th}$ Edition), Entry 4685, 1996.

Moczar et al., "Biocompatibility of a Vascular Substitute from Heparinized Human Umbilical Cord Vein", Life Support System, 1986, pp. 103-105, vol. 4, Suppl. 2.

Ip et al., "Patency of Heparin-PVA Coated Tubes at Low Flow Rates", Biomaterials, 1989, pp. 313-317, vol. 10, No. 5, Elsevier Science, London, England.

* cited by examiner

HEPARIN-LIKE COMPOUNDS, THEIR PREPARATION AND USE TO PREVENT ARTERIAL THROMBOSIS ASSOCIATED WITH VASCULAR INJURY AND INTERVENTIONS

This application is a divisional of U.S. application Ser. No. 09/230,097, filed on Jan. 20, 1999 now abandoned, which was a national stage filing under 35 U.S.C. § 371 of International Application No. PCT/FI98/00925 filed on Nov. 25, 1998.

THE TECHNICAL FIELD OF THE INVENTION

The invention is related to heparin-like compounds characterized by their capacity of almost complete inhibition of collagen-induced platelet aggregation in flowing whole blood and a coupling density of negatively charged heparin or heparin-like glycosaminoglycan units that gives them the unique properties first displayed in native mast cell-derived heparin proteoglycans (HEP-PG) or heparin glycosaminoglycan (HEP-GAG) molecules-obtainable thereof. The present invention is also related to methods for preparing said heparin-like compounds and their use in prophylactic treatment of arterial thrombosis associated with vascular injuries and interventions.

THE BACKGROUND OF THE INVENTION

Heparin is a glycosaminoglycan, an acidic mucopolysaccharide composed of D-glucuronic acid and D-glucosamine with a high degree of N-sulphation. It is present in the form of proteoglycan in many mammalian tissues, such as the intestine, liver, lung, being localized in the connective tissue-type mast cells, which line for example the vascular and serosal system of mammals. The main pharmaceutical characteristic of heparin is its ability to enhance the activity of the natural anticoagulant, antithrombin III.

Heparins exist naturally bound to proteins, forming so called heparin proteoglycans. Usually, the endogenous or native, naturally existing heparin proteoglycans contain 10-15 heparin glycosaminoglycan chains, each chain having a molecular weight in the range of 75±25 kDa, and being bound to one core protein or polypeptide. Each native heparin glycosaminoglycan chain contains several separate heparin units consecutively placed end-to-end, which are cleaved by endoglycosidases in their natural environment. The natural or native conjugates are difficult to prepare in pure form. Thus, they have not been suggested for therapeutical or corresponding use. Heparin glycosaminoglycans belong to a larger group of negatively charged heteropolysaccharides, which generally are associated with proteins forming so called proteoglycans. Examples of other naturally existing glycosaminoglycans are for example chondroitin-4- and 6-sulphates, keratan sulphates, dermatan sulphates, hyaluronic acid, heparan sulphates and heparins. Of said heparin-like compounds existing in nature, only hyaluronic acid is generally not associated with a proteinaceous core molecule.

During the past decades the trend in heparin research has been to develop and use heparin chain units, which have been fractionated for systemic clinical preparations of shorter chains to increase specificity. The generally used two types of standard clinical heparins are the so called unfractionated or high-molecular weight heparins and fractionated or low-molecular-weight heparins. Said two types of heparins have an average molecular weight of 15 and 5 kDa, respectively. In the present invention these two types of heparins are both considered to be lower-molecular-weight heparins. Most commercial preparations have a molecular weight between 4 to 20 kDa depending on their origin, the method of preparation and/or determination. Thus, the commercial heparins belong to the lower-molecular-weight heparins as defined in the present invention.

In the U.S. Pat. No. 5,529,986 a synthetic macromolecular heparin conjugate is described. It consists of at least 20 heparin moieties, but can contain more than 100 heparin moieties, combined with natural or synthetic substantially straight-chained polymer backbones such as polylysine, polyornithine, chitosan, polyamine or polyallyl.

However, in said patent each heparin moiety is also characterized by a low molecular weight of approximately 12 kDa, which is far shorter than the heparin chains in native heparin proteoglycans. The macromolecular heparin molecule described in U.S. Pat. No. 5,529,986 is said to be especially useful for coating surfaces in extracorporeal circulation systems and its action is said to be based on binding to antithrombin III and enhancement of its activity, which is the main functional anticoagulant mechanism of all current heparin preparations.

Primarily, the standard heparin preparations are used for systemic treatment of thrombosis. As such they are most efficient in platelet-poor thrombi, such as venous thrombi, where coagulation activity prevails. The clinically used standard heparins, though effective in systemic treatment of thrombosis, by blocking the further growth of thrombosis, are not effective enough to prevent thrombotic complications, associated with either endogenous rupture of an atheromatous plaque or exogenous angioplasty or vascular or microvascular surgery.

Arterial interventions, such as angioplasty [PT(C)A=percutaneous transluminal (coronary) angioplasty] with or without stenting and vascular or microvascular surgery as well as (directional) arterectomy and peripheral thrombendarterectomy, represent a growing modality of treatment for cardiovascular diseases, which are the main cause of death. Accordingly, platelet-driven arterial thrombosis, which occurs in connection with endogenous vascular or microvascular injuries and/or exogenous interventions is a frequently encountered problem and in these situations the traditional systemic treatment of thrombosis is often of limited efficacy.

Current systemic antithrombotic treatment in connection with arterial interventions include the combination of an anticoagulant, such as unfractionated heparin (12 kDa) or low-molecular-weight heparins (7.5 kDa) with an antiplatelet drug, such as acetylsalicylic acid (cyclooxygenase inhibitor), or ticlopidine or better clopidogrel (ADP antagonist). The latest development is represented by potent platelet glycoprotein IIb/IIIa, von Willebrand factor and fibrinogen receptor antagonists, such as abciximab, tirofiban and velofibatide. The new combination treatments have succeeded in preventing 30-35% of acute thrombotic closures of the interventionally treated thrombus-prone vessels. The bleeding risk (major bleeding) requiring infusion of blood products is around 6-7%. So far abciximab has had the best efficacy, but since it is an antibody-based drug repetitive administration may cause antigenicity.

The systemic treatment with unfractionated heparin suffers from many unwanted effects, such as unpredictable bioavailability, short half-life, unspecific binding to proteins leading to compromised antithrombin III function and immunologic platelet effects with thrombocytopenia and thrombosis as well. These unwanted effects have been largely bypassed with the use of the low-molecular-weight, fractionated heparins, which however, have a limited capacity in inhibiting arterial thrombosis due to a limited control of fibrin-bound thrombin, and of platelet-bound factor Xa, and due to the neutralization of heparin-activity by platelet-secreted platelet factor 4. Thus, there is a great need for developing an effective and reliable prophylactic treatment of arterial thrombosis associated with vascular or microvascular injuries and interventions.

In their studies, the present inventors found that in contrast to the lower-molecular-weight heparins, native heparin proteoglycans (HEP-PG) obtainable from mammalian mast cells express potent antithrombotic properties, which are based on their capacity to inhibit platelet-collagen interactions. This unique property, namely blocking the platelet activation events subsequent to platelet adhesion to collagen, which is not present in the lower-molecular-weight, including unfractionated and fractionated commercial heparins, occurs simultaneously with a potential to enhance the function or activity of antithrombin III or heparin cofactor II.

In contrast to the traditional heparin mechanism, i.e. the antithrombin III enhancing action of heparins in the current clinical use as well as that of the macromolecular heparin construct described in U.S. Pat. No. 5,529,986, the efficacy of the heparin-like compounds of the present invention does not depend on the antithrombin III activity, but is based on a previously undescribed mechanism of strong inhibition of platelet activation triggered by platelet adhesion upon collagen. The exact mechanism is presently unknown, but is supposed to depend on disruption of the activation signal following platelet GP Ia/IIa binding to collagen and subsequent membrane phospholipid flip-flop and procoagulant activity, normally induced by collagen in platelets. Also, strong binding to von Willebrand factor (vWF) may be involved.

The present invention provides an alternative for anti-platelet treatment in form of local application, which can be combined with a systemic antiplatelet drug. This combination can be used in conjunction with angioplasty, vascular and microvascular surgery and endarterectomy to passivate the exposed subendothelial vascular and microvascular collagen for adhering platelets. During the initial studies, the desired effect achieved with the heparin proteoglycans (HEP-PG), was a significantly reduced local thrombus formation based on inhibition of platelet-to-platelet interaction, but preserved adhesion upon collagen. The collagen-induced platelet activation upon the adherent platelets was shown to be fully blocked in the presence of mast cell-derivable heparin proteoglycans (HEP-PG), multiple heparin glycosaminoglycan molecules, as such or connected to core molecules and lower-molecular-weight heparin or heparin-like glycosaminoglycans connected to spheroidal or globular core molecules to provide the spatially optimal macromolecular presentation or configuration which provides a sufficient coupling density of negatively charged glycosaminoglycans.

The above defined effect was obtainable both when the heparin glycosaminoglycan (HEP-GAG) having a molecular weight of 75±25 kDa and/or multiple carrier-(core molecule) coupled, spacer/linker-provided, unfractionated or fractionated heparin or heparin-like chains presented in the optimal spatial configuration and proteoglycan (HEP-PG) molecules comprising said HEP-GAG-molecules were in solution or immobilized on collagen-coated surfaces or administrated to vessel surfaces to be closed as anastomosis. Thrombin targeting with the current means to prevent thrombosis and to limit excessive wound repair, has still been associated with development of restenosis at the treated site. The advantage of the HEP-GAG- and HEP-PG-molecules of the present invention was preserved systemic platelet function which ensured normal hemostatic responses. The local inhibitory effect of mast cell-derived HEP-GAG- and HEP-PG-molecules on smooth muscle cell proliferation in vitro was also shown to be significantly better than that of lower-molecular-weight heparin species (Wang & Kovanen, Circulation Res, In Press).

Based on these preliminary findings the present inventors developed the heparin-like compounds of the present invention, as well as methods for their preparation and their use. The objectives of the invention are set forth below.

The first objective of the present invention was to provide soluble heparin-like compounds, mimicking the structure and properties of the mast cell-derived multiple heparin glycosaminoglycans (HEP-GAG) and/or heparin proteoglycans (HEP-PG), which HEP-GAG- and HEP-PG-molecules had been shown to be characterized by a hitherto unreported mechanism based on an almost complete inhibition of platelet-collagen interaction. Said mechanism is useful and convenient for screening and determining the properties of newly developed, synthetically, semisynthetically or biotechnologically modified heparin-like compounds as well as of locally applicable preparations useful for preventing thrombosis associated with vascular or microvascular injuries and interventions, such as angioplasty, stenting and vascular grafting.

Another objective of the invention was to provide pharmaceutically useful preparations, which comprise the heparin-like compounds of the present invention in combination with compatible adjuvants, carriers, etc.

A third objective of the invention was to provide means for and/or devices for administering the heparin-like compounds of the present invention by coating said means or devices.

The objective of the invention was also to provide methods for preparing said HEP-GAG- and HEP-PG-molecules from mast cells and to further modify the mast cells or the HEP-GAG- or HEP-PG-molecules by chemical and/or biotechnological methods to provide novel heparin-like compounds, with optimal spatial configurations and properties which are defined in the claims and which are similar to those of the native mast cell-derivable HEP-PG-molecules or the multiple HEP-GAG-molecules obtainable therefrom.

Still a further objective of the present invention was the use of the heparin-like compounds of the present invention as such or as ingredients for manufacturing preparations and devices useful for prophylactic treatment and prevention of severe vascular disorders including arterial thrombosis in connection with vascular and microvascular surgery or interventions, such as angioplasty, stenting and vascular grafting.

THE SUMMARY OF THE INVENTION

Platelet-collagen interactions are the essential triggering event in hemostasis and developing arterial thrombosis. In their preliminary studies, the inventors found that there is a clear connection between the molecular weight of the heparin proteoglycans (HEP-PG)—especially the high molecular weight of the heparin proteoglycans (HEP-PG) based on the multiple structure or the spatial configuration or presentation of its heparin glycosaminoglycan (HEP-GAG) moieties—and their inhibitory effects on platelet-collagen interaction. It was shown that the best results were obtainable with multiple glycosaminoglycans (HEP-GAG) or heparin proteoglycans (HEP-PG) containing multiple HEP-GAG chains having a size, which mimicks the situation in vivo, wherein vascular mast cells were activated and excreted their granules into the external body fluids, wherein the granulate-derived heparin molecules solubilized. Said solubilized heparin proteoglycans (HEP-PG) contained in average about 10 heparin glycosaminoglycan (HEP-GAG) moieties, each with a molecular weight of 75±25 kDa. The desired effect was also obtained by combining several unfractionated or fractionated, herein so called lower-molecular-weight heparin glycosaminoglycan units end-to-end or end-to-side to form multiple glycosaminoglycans, either as such or connected to core molecules. Also similar inhibition of aggregation was found, when multiple aminosulphated groups of multiple unfractionated heparin chains (12±10 kDa) were coupled with a heterobifunctional coupling reagent, i.e. a spacer or linker molecule, such as N-succinylimidyl-3(2-pyridylthio)propionate (SPSD) to lysine residues present in albumin, a globular protein, offering an optimal core molecules for producing the optimally charged heparin-like compounds of the present invention with the spatial configuration and coupling density.

Thus, the present invention is related to heparin-like compounds, which comprise multiple heparin or heparin-like glycosaminoglycan molecules, which have a high molecular weight and consist of several end-to-end and/or end-to-side connected heparin or heparin-like glycosaminoglycan molecules as such or connected to a natural or synthetic, chain-like, preferably short or globular core molecule or lower-molecular-weight heparin or heparin-like glycosaminoglycans conjugated to a globular core molecule. Preferably, spacer or linker molecules, which allow attachment of more heparin or heparin-like molecules than the core molecules themselves are used to provide, the desired, sufficient coupling density of said heparin or heparin-like glycosaminoglycan molecules. The heparin-like compounds of the present invention, advantageously, have a coupling density of negatively charged heparin or heparin-like glycosaminoglycan molecules or units, which provides the heparin-like compounds of the present invention with a spatial configuration, which seems to be responsible for or closely related to the unique and specific properties of the heparin-like compounds of the present invention and which properties were first recognized with the mast cell-derived HEP-GAG- and HEP-PG-molecules, said property being the capacity of substantially complete inhibition of the platelet aggregation upon collagen in flowing blood, which is a general cause of arterial thrombosis associated with vascular or microvascular injury and interventions.

The heparin-like compounds of the present invention preferably comprise several multiple end-to-end and/or end-to-side connected heparin glycosaminoglycan (HEP-GAG) molecules. Each of which should preferably have a molecular weight of 75±25 kDa or more than 75±25 kDa.

In the heparin-like compounds of the present invention the multiple heparin or heparin-like glycosaminoglycan molecules can be connected, coupled or conjugated to a natural or synthetic core molecule, which preferably is globular or provides the desired spheroidal configuration, but they can also be connected to more chain-like core molecules.

Also lower-molecular-weight heparin or heparin-like glycosaminoglycan molecules can be connected to core molecules. However, in such cases the core molecule should have a spheroidal or globular configuration. It is also recommendable to use spacer or linker molecules, which allow coupling of much more heparin or heparin-like molecules or units and thus provides a more optimal spatial configuration and a higher coupling density.

The core molecules are advantageously proteins or polypeptides. Useful examples of core molecules are globular proteins, such as albumin, preferably serum albumin of human origin. Another type of core molecules is a polypeptide, which need not be very long and comprises e.g. one or more repetitions of the Ser-Gly-Ser-Gly- sequence. Alternatively, other kinds of amino acid sequences can be used.

The present invention describes methods for producing the heparin-like compound both from natural sources, synthetically or semisynthetically or by biotechnological methods, including genetical modifications from commercially available heparins and proteins or polypeptides.

Natural heparin-like compounds are prepared by allowing isolated and purified connective tissue-derived mast cells to grow in a suitable cell culture medium using conditions allowing good cell proliferation and production of heparin-containing granules. After the growth step has been completed, i.e. when the yields of the heparin proteoglycans are optimal, the heparin proteoglycan-containing granules are released by optional activation and/or lysis. The activation step can be carried out with mast cell agonists, which induce mast cell degranulation and release solubilized, multiple HEP-PG-molecules. Preferred agonists are selected from a group consisting of basic polyamines and calcium ionophores. The released granules are allowed to solubilize in the surrounding culture medium and said solubilized heparin proteoglycan (HEP-PG) is collected from the exterior medium. Thereafter, if desired, native multiple heparin glycosaminoglycans (HEP-GAG) can be separated from said heparin-proteoglycans and said heparin glycosaminoglycan (HEP-GAG) molecules can be further coupled to each others in order to obtain heparin glycosaminoglycans with a higher degree of branching and/or multiplicity.

In the synthetic or semisynthetic methods several heparin or heparin-like glycosaminoglycan units can be connected end-to-end and/or end-to-side by covalent bonds. Optionally, especially when using lower-molecular-weight heparin molecules as starting material, coupling reagents, such as spacer or linker molecules, should be used to provide the optional multiplicity and spatial configuration.

The present invention is above all related to a method for prophylactic treatment of arterial thrombosis associated with vascular or microvascular injuries and/or interventions. The method is performed by local administration of the heparin-like compounds of the present invention. The local administration is performed by directly applying an effective amount of the heparin-like compounds of the present invention in the form of preparations and/or indirectly as devices, such as stents, vascular grafts or extracorporeal circulation systems coated with the heparin-like compounds of the present invention. The heparin-like compounds of the present invention can be combined with pharmaceutically acceptable carriers and/or adjuvants to provide more advantageous preparations for application and administration.

The present invention also describes preparations, means and/or devices for local administration of the heparin-like compounds of the present invention in connection with vascular or microvascular injuries or interventions. Effective local administration is obtained for example by means and/or devices coated with heparin-like compounds of the present invention.

The invention is also related to a method for preventing platelet aggregation or clogging at the site of vascular injury or intervention. The prevention is obtainable especially by the aid of devices coated with the heparin-like compounds of the present invention.

Methods for manufacturing means and/or devices for local administration are also suggested and include for example contacting the devices with a solution containing the heparin-like compounds of the present invention and treating the devices appropriately under sterile conditions, so that the activity is retained and storing is possible. The devices can for example be dried, e.g. by lyophilization and stored in sterile vials until used. Other ways of treating and storing the devices coated with the heparin-like compounds of the present invention are known to those skilled in the art.

The present invention is thus related to the use of heparin-like compounds for manufacturing medicines and/or devices capable of substantially complete inhibition of platelet aggregation upon collagen in flowing whole blood, the cause of arterial thrombosis associated with vascular or microvascular injury and interventions.

THE SHORT DESCRIPTION OF THE FIGURES

Figure 3:
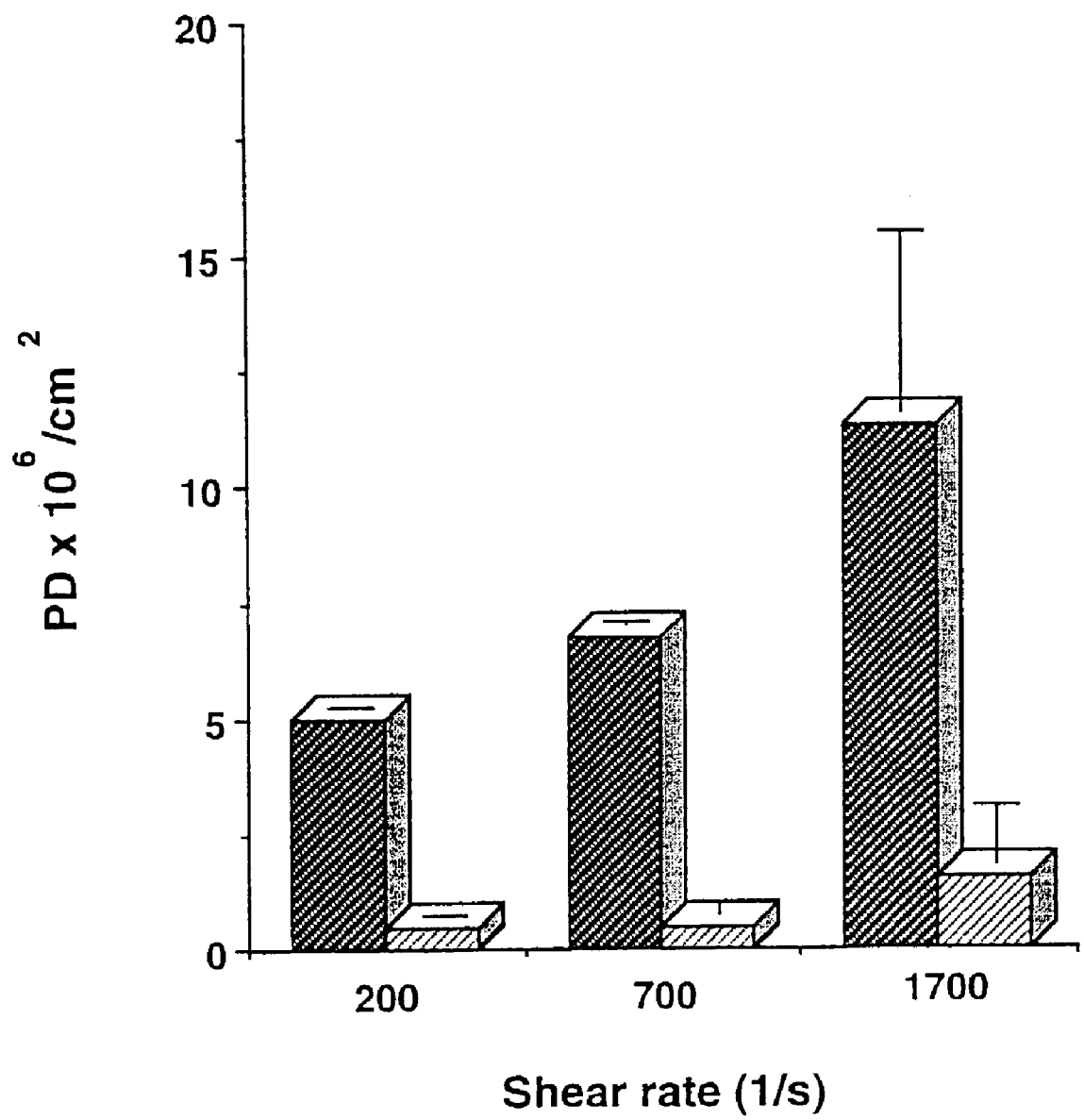

FIG. 3 shows the effect of mast cell-derived HEP-PG (3 µg/ml) on platelet deposition on collagen (bovine, type I, fibrillar) under different shear rate conditions in PPACK-anticoagulant flowing whole blood. Perfusion time was 5 minutes. Values are means±SD for four donors at 200, 700 and 1700 1/s, all in duplicate.

Figure 4:
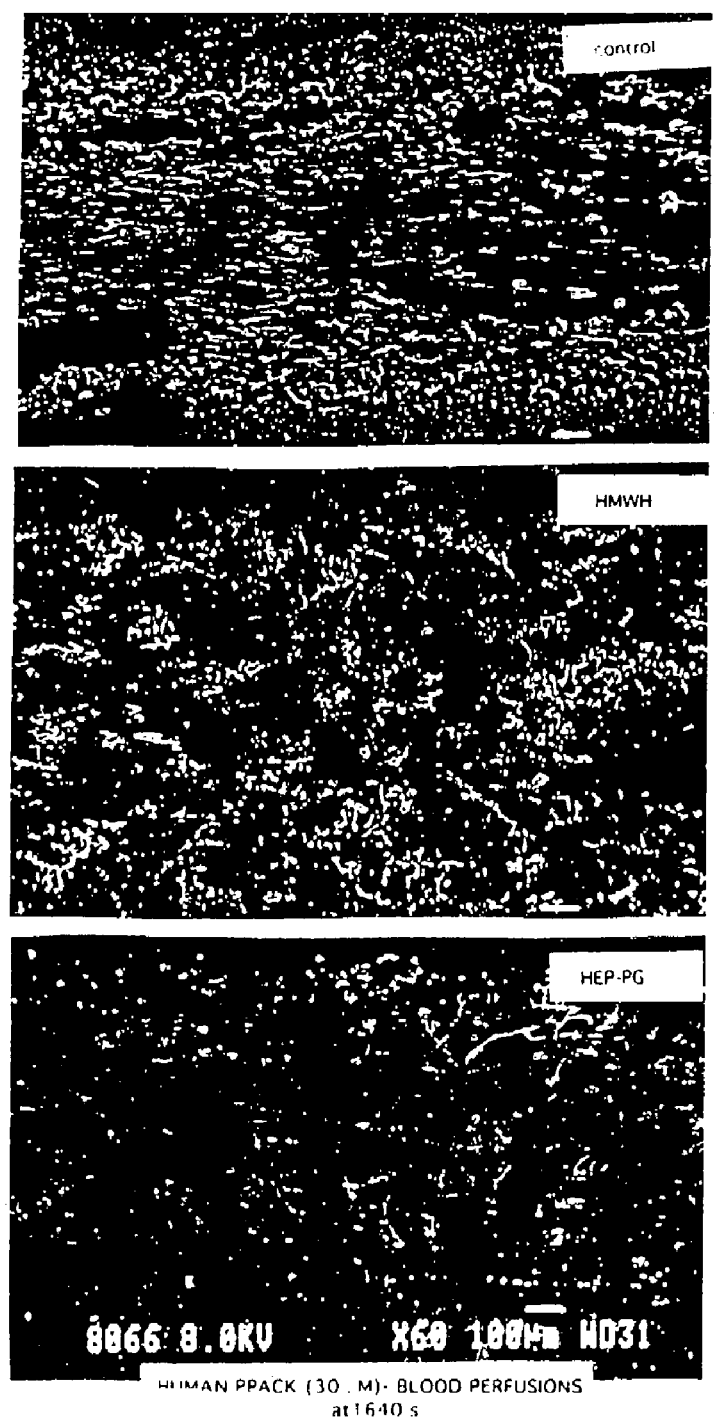

FIG. 4 shows scanning electron micrographs of perfusion channels with immobilized standard heparin (10 mg/ml) or mast cell-derived HEP-PG (10 µg/ml) after human whole blood perfusions over monomeric collagen type I under the shear rate of 1640 I/s. In the top panel, control, large platelet aggregates can be detected in the perfusion channel. In the middle panel standard unfractionated heparin (HMWH) somewhat reduced the size of aggregates, but did not seemingly affect surface coverage. In the lower panel, in the presence of mast cell-derived HEP-PG, platelet deposition was almost absent, only occasional adherent single platelets, mainly in the channel edges having the low shear rate conditions, were detected.

Figure 5:
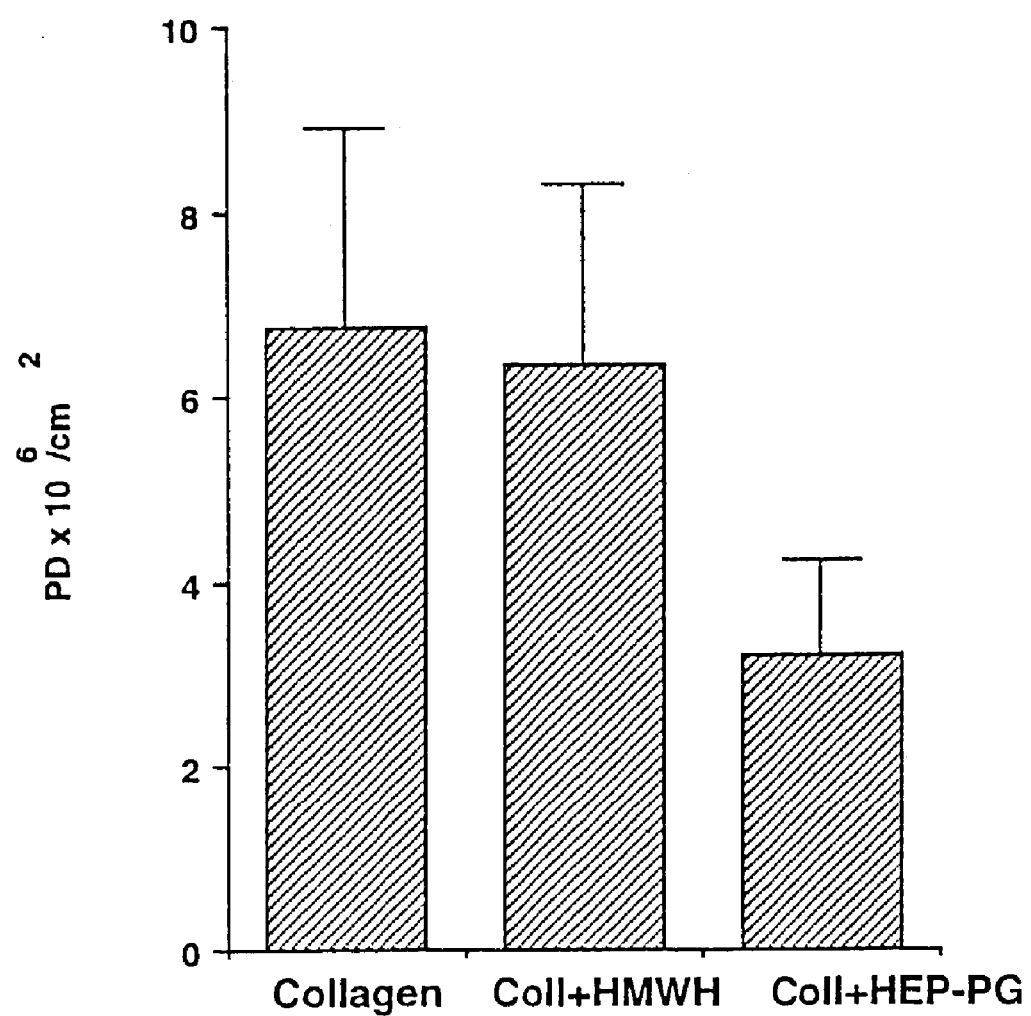

FIG. 5 shows the effect of immobilized unfractionated standard heparin (10 mg/ml) and HEP-PG (10 µg/ml) on platelet deposition over collagen type I in fibrillar form (equine, Horm™ collagen Nycomed). Platelet deposition to this form of collagen is dependent on GP IV and GP VI in addition to GP Ia/IIa. Donors are five, all duplicate. Shear rate was 1640 I/s, perfusion time was 5 min and blood was anticoagulated with PPACK 30 µM. Coll is collagen and HMWH is unfractionated standard heparin and HEP-PG is mast cell-derived heparin proteoglycan.

Figure 6:
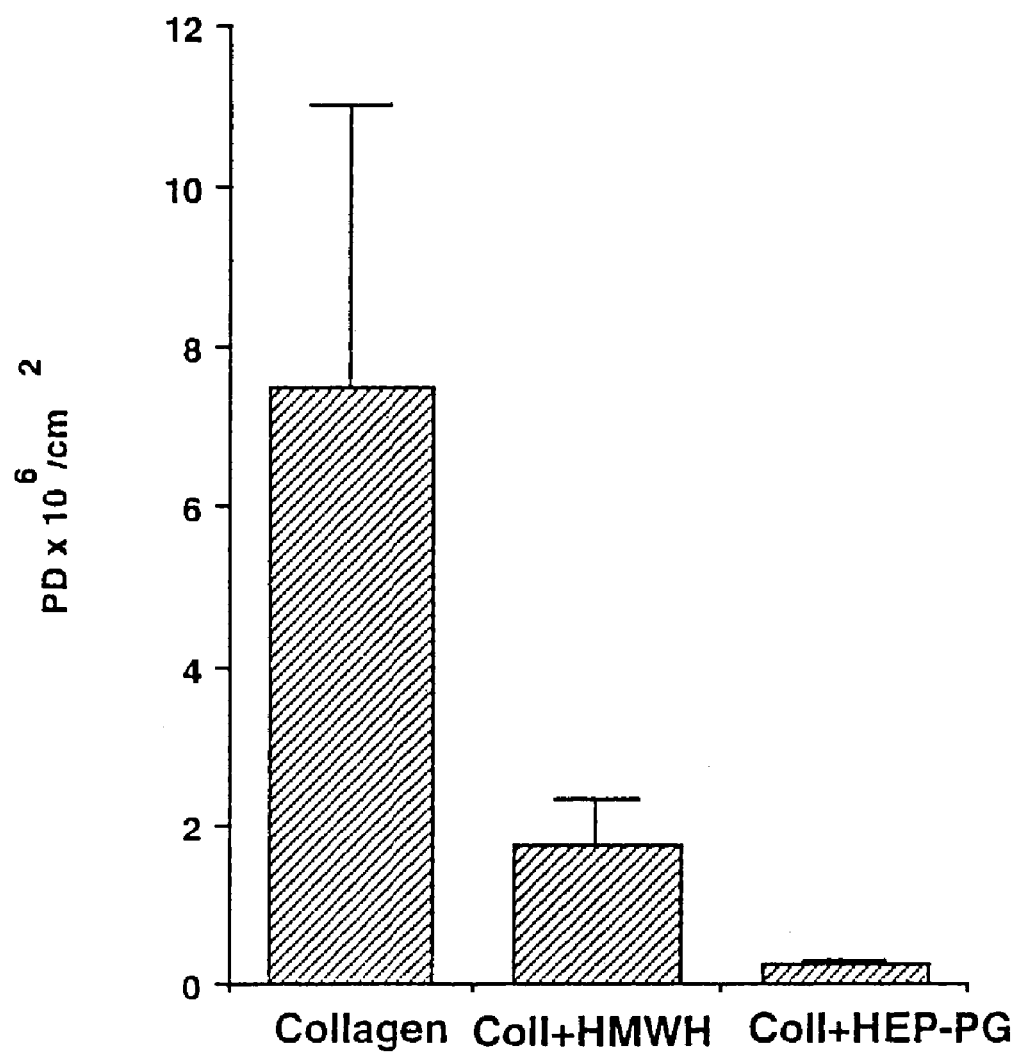

FIG. 6 shows the effect of immobilized unfractionated standard heparin (10 mg/ml) and mast cell-derived HEP-PG (10 µg/ml) on platelet deposition over collagen type I in monomeric form, native acetic acid-soluble bovine collagen fibers digested with pepsin. Platelet deposition is highly dependent on GP Ia/IIa. Both unfractionated heparin and HEP-PG inhibited platelet deposition when immobilized or monomeric collagen, however, HEP-PG was significantly more potent in its inhibitory function. Donors are five, all duplicate. Shear rate was 1640 I/s, perfusion time was 5 min and blood was anticoagulated with PPACK 30 µM. Coll is collagen and HMWH is unfractionated, standard heparin and HEP-PG is mast cell-derived heparin proteoglycan.

Figure 7:
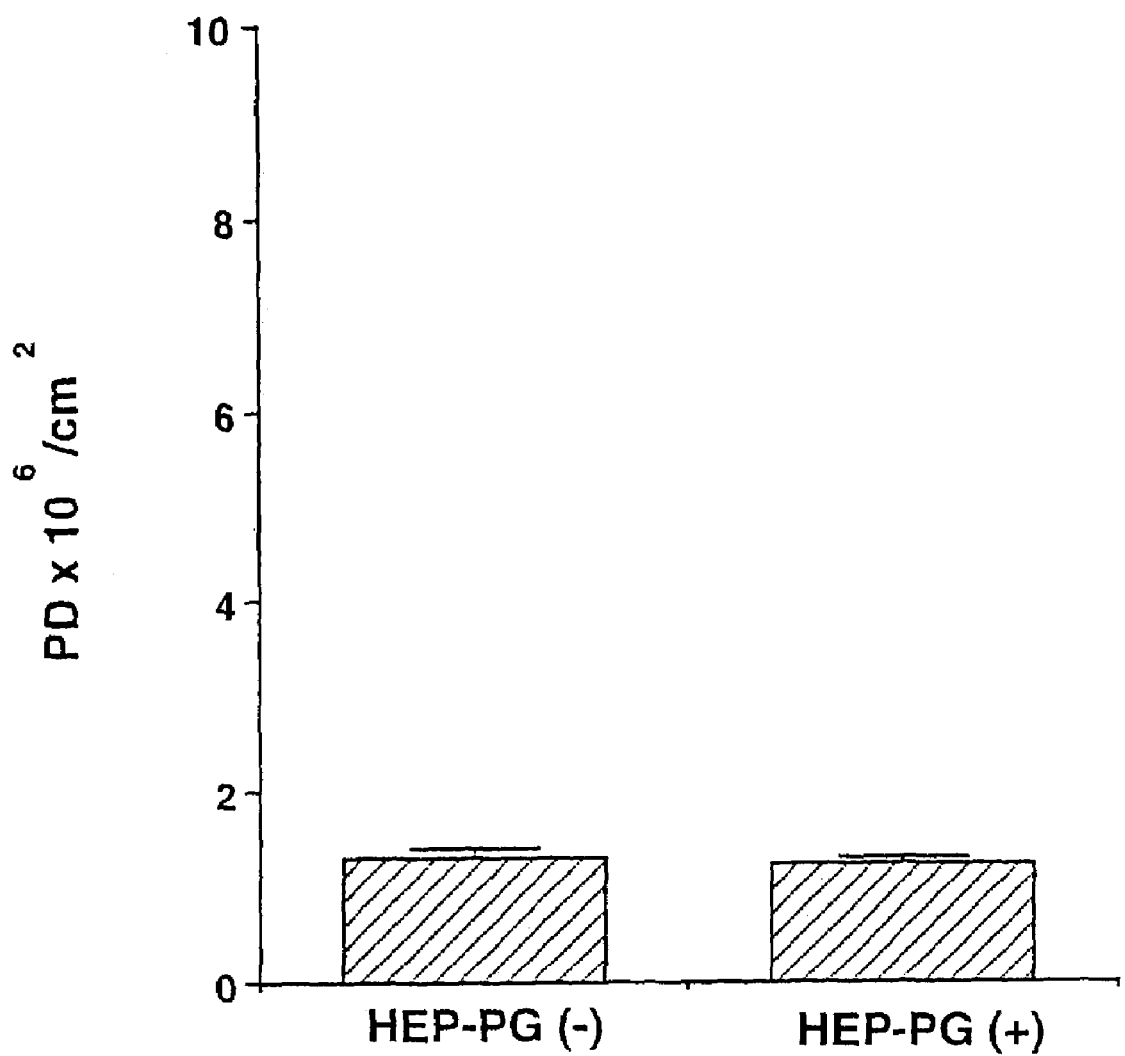

FIG. 7 shows the effect of mast cell-derived HEP-PG on platelet interaction with fibrillar type I collagen in Mg2+ (2 mM)-containing buffer. The experiment comprised 100× $10^6$/ml platelets at 22° C. under static conditions leading to equal platelet adhesion. Data are means±SD of values for four donors, all in duplicate. PD is platelet deposition.

Figure 8:
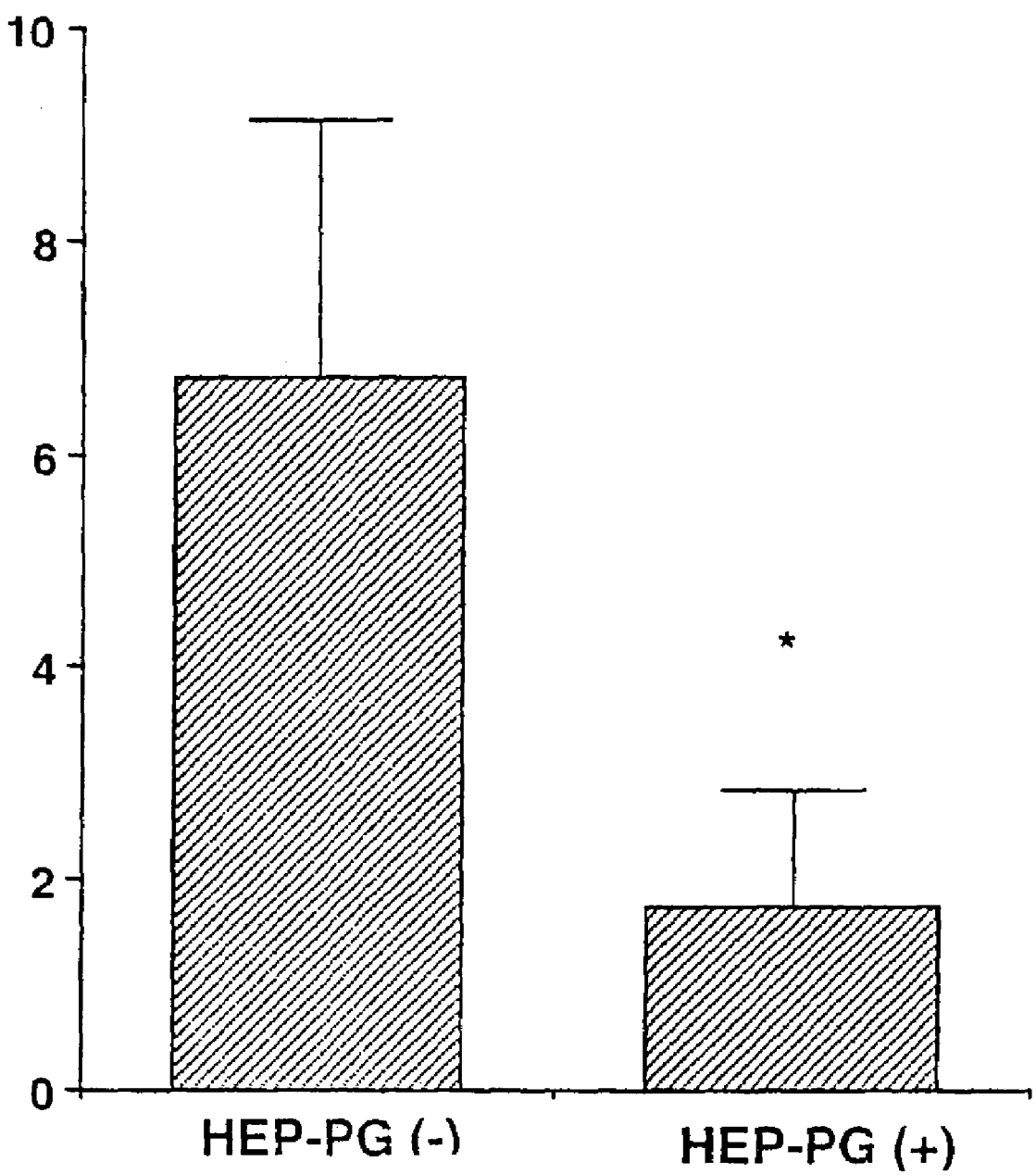

FIG. 8 shows the effect of mast cell-derived HEP-PG on platelet interaction with collagen in Mg2+ (2 mM)-containing buffer. The experiment comprised 300×$10^6$/ml platelets at 37° C. under slow rotation (100 rpm) permitting platelet interaction on fibrillar type I collagen-adherent platelets. Data are means±SD of values for five donors, all in duplicate. *$p<0.0001$, paired t-test. PD is platelet deposition.

Figure 9:
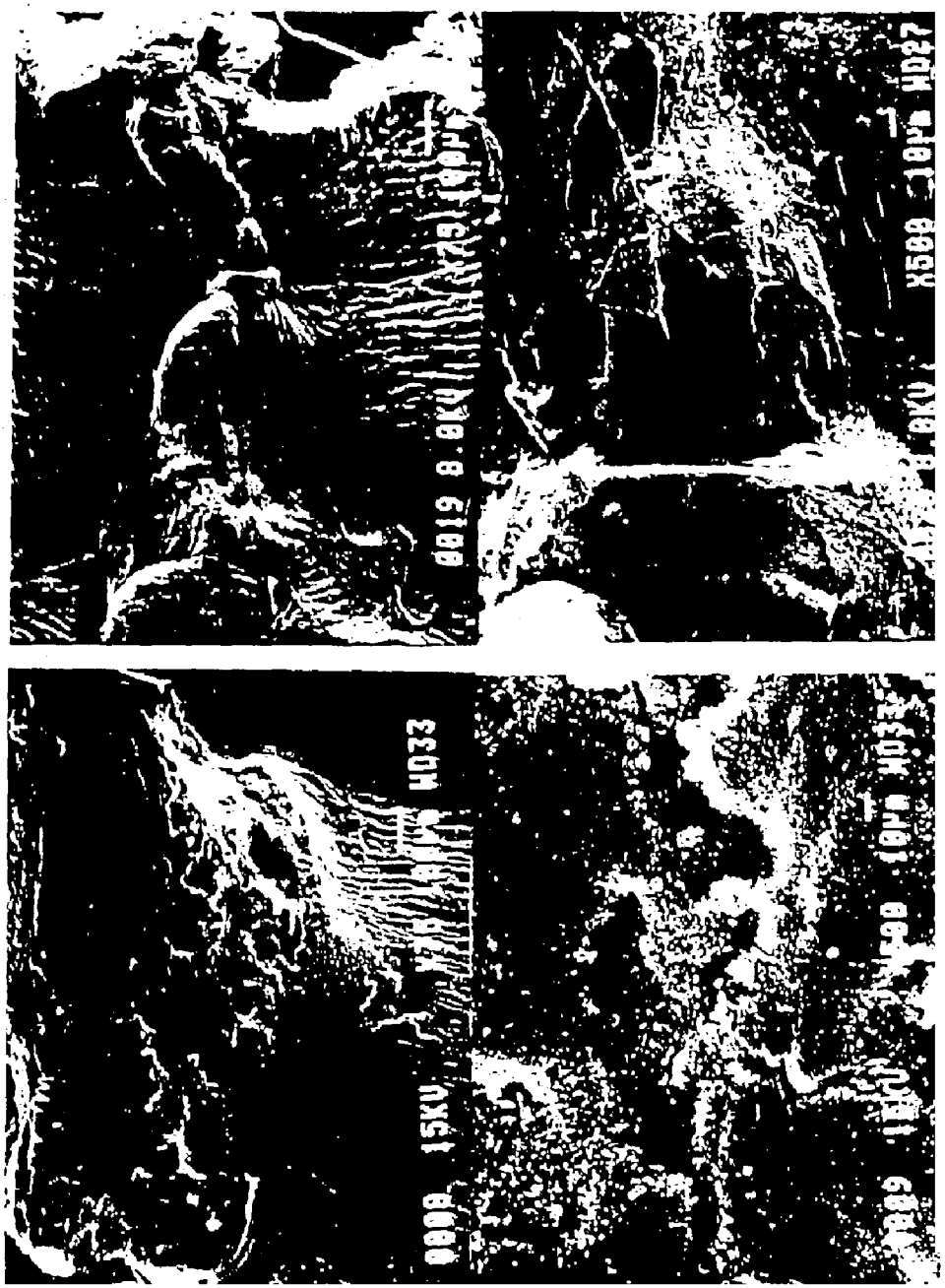

FIG. 9 shows scanning electron micrographs of the rat anastomosis model after 10 minutes circulation of blood over the vessel. Two magnifications, ×75 and ×500 of the perfused anastomosis area. The left-sided panels represent saline-treated anastomosis and the right-sided panels represent mast cell-derived HEP-PG-treated anastomosis. These experiments are representative of 5 different experiments.

FIG. 10A shows the collagen-induced (Sigma, aggregation kit, at 25 µg/ml) platelet aggregation in citrated PRP.

FIG. 10B shows the effect of mast cell-derived HEP-PG (at 3 µg/ml of heparin) on collagen-induced platelet aggregation.

FIG. 10C shows the effect of albumin-coupled unfractionated heparin (at 0.75 µg/ml of heparin) on collagen-induced platelet aggregation).

THE DETAILED DESCRIPTION OF THE INVENTION

Definitions

In the present description the following abbreviation and acronyms are frequently used. GP means glycoprotein. HEP-GAG means long (75 kD) or branched or multiple heparin glycosaminoglycans, which are capable of almost complete inhibition of collagen-induced platelet aggregation in flowing whole blood. HEP-PG means heparin proteoglycans (natural or synthetic or semisynthetic and core molecule-coupled, i.e. protein- or peptide-coupled) comprising the above defined HEP-GAG molecules. HMWH means commercially available, unfractionated high-molecular-weight, 7.5-30 kDa heparins or heparin glycosaminoglycan units. LMWH means commercially available, low-molecular-weight, less than 7.5 kDa heparins or heparin glycosaminoglycan units. Said two types of heparins are in the present invention so called lower-molecular-weight heparin molecules or units. HSA means human serum albumin, BSA means bovine serum albumin and MW molecular weight. PBS means phosphate-buffered saline, PPACK D-phenylalanyl-1-propyl-1-arginine chloromethyl ketone, PRP platelet-rich plasma, SDS sodium dodecyl sulfate, TES N-Tris (hydroxy-methyl)methyl-2-aminoethane sulfonic acid and vWf von Willebrand factor. SPDP means N-succinylimidyl-3-(2-pyridylthio)propionate.

In the present description the terms used have the same meaning as they generally have in medical sciences, including immunochemistry, immunology, biochemistry, etc., as set forth in textbooks and review articles in said fields. Some terms are, however, used more extensively and have a meaning that somewhat differs from the general use of the term. Some of these terms are defined below.

The term "heparin-like compound" means compounds which have a structure resembling that of mast cell-derived heparin proteoglycans and heparin glycosaminoglycans and which are characterized by their capacity of almost complete inhibition of collagen-induced platelet aggregation in flowing whole blood and a coupling density of negatively charged heparin or heparin-like glycosaminoglycan units that gives them the unique properties displayed by the native mast cell-derived heparin proteoglycans (HEP-PG) or heparin glycosaminoglycan (HEP-GAG) molecules obtainable thereof and which property can be measured by the method(s) described in Lassila R, Lindstedt K, Kovanen P T. Arteriosclerosis, Thrombosis, and Vascular Biology 1997; 17 (12): 3578-3587.

The heparin-like compounds of the present invention, either soluble or immobilized on collagen, are above all characterized by their capacity for inhibiting the platelet aggregation upon collagen in flowing whole blood, which is a cause of arterial thrombosis associated with vascular injury and interventions as well as their capacity for preventing the interaction of flowing whole blood with collagen. Said properties, in addition to the multiple structure or the optimal coupling density of the heparin or heparin-like glycosaminoglycan molecules, are the prerequisites required of the heparin-like compounds of the present invention.

In its most specific meaning the term "heparin-like compounds" is limited to mast cell-derived heparin proteoglycans (HEP-PG) and heparin glycosaminoglycans (HEP-GAG) obtainable thereof. However, it also includes multiple, unfractionated or fractionated heparin or heparin-like chains coupled to core molecules, either directly or by aid of spacer or linker molecules to provide heparin-like compounds with a unique, spatially optimal configuration, which provides the compounds with a desired, high coupling density of negatively charged heparin or heparin-like glycosaminoglycan molecules or units. The desired high coupling density which provides the unique properties of the heparin-like compounds of the present invention was first found for example in native mast cell-derived heparin proteoglycans (HEP-PG) or the multiple heparin glycosaminoglycan (HEP-GAG) molecules and it seems to explain their properties as well.

The term "heparin or heparin-like proteoglycan" in the present invention means such heparin or heparin-like proteoglycans, which fulfill the prerequisites set up in the definition of heparin-like compounds. Preferably the proteoglycans contain more than three multiple heparin or heparin-like glycosaminoglycan molecules bound to a core molecule. The term "heparin or heparin-like compounds" above all covers native, water-soluble heparin proteoglycans (HEP-PG) obtainable from mammalian connective tissue type mast cells, either by tissue extraction or preferably by cell cultivation. These heparin proteoglycans (HEP-PG) usually comprise approximately 10-15 multiple heparin glycosaminoglycan (HEP-GAG) molecules. Synthetically produced heparin or heparin-like proteoglycans can comprise any number of multiple heparin or heparin-like glycosaminoglycan molecules as long as they fulfill the above defined prerequisites.

The term "water-soluble or solubilized heparin-like compounds" means that the mast cell-derived HEP-PG-molecules are released from the granules of the mast cells into the exterior medium in which they solubilize and thereafter can be separated from cell debris and other non-soluble components. It is to be observed that the other heparin-like compounds of the present invention should be provided with the same type of solubility as defined above, even if it is an inherent property of all said molecules to easily adhere to certain, especially solid surfaces.

The term "multiple heparin or heparin-like glycosaminoglycan molecule" above all includes the native heparin glycosaminoglycan (HEP-GAG) molecules obtainable from the mast cell-derived heparin proteoglycans and having a molecular weight of 75±25 kDa. The term also includes synthetically or semisynthetically obtainable heparin or heparin-like glycosaminoglycans with several end-to-end and/or end-to-side coupled glycosaminoglycan units, obtainable for example from unfractionated or fractionated lower-molecular-weight heparins. Said "multiple heparin or heparin-like glycosaminoglycan molecules" form multiple straight or branched molecules with the properties set forth in the definition of heparin-like compounds. Each heparin or heparin-like glycosaminoglycan molecule should have a sufficient molecular weight to provide the properties set out in the definition of the heparin-like compounds.

The "multiple heparin or heparin-like glycosaminoglycan molecules" or unfractionated or fractionated heparin or heparin-like chains can be conjugated to natural, synthetic or semisynthetic core molecules, for example proteins, preferably globular proteins to provide heparin proteoglycans with the properties defined above.

The term "multiple heparin or heparin-like glycosaminoglycan molecules" include molecules having for example at least 3-4 end-to-end or end-to-side connected heparin or heparin-like glycosaminoglycan units, each having a molecular weight corresponding to the commercially available unfractionated or fractionated lower-molecular-weight heparins. Their molecular weight is generally less than 20 kDa, mostly less than 15 kDa but also heparin glycosaminoglycans with molecular weight of less than 12 kDa can be used. In such case, only more of them have to be combined in order to give the HEP-GAG-molecules which have a sufficiently high MW or coupling density to provide the properties defined in connection with the heparin-like compounds. Native mast cell-derived naturally multiple heparin glycosaminoglycan (HEP-GAG) molecules generally have a molecular weight of about 75±25 kDa. Such natively "multiple heparin glycosaminoglycan molecules" can also be coupled end-to-end and/or end-to-side in order to give larger molecules, which also belong to the scope of the present invention. Thus, the multiple heparin glycosaminoglycan (HEP-GAG) molecules of the present invention have a molecular weight of at least 75±25 kDa, including any multiples thereof. Heparin-like glycosaminoglycans do not necessarily have to have the defined molecular weight, if they otherwise have the characteristic features of heparin-like compounds as defined in the claims. In addition, to the high molecular weight, an alternative way of providing sufficient coupling density is provided by coupling unfractionated or fractionated glycosaminoglycans, e.g. heparins to globular core molecules. The desired density is especially obtainable by using specific spacer or linker molecules, which allow the binding of much more of the desired heparin or heparin glycosaminoglycan units.

Even if the native mast cell-derived HEP-GAG- and HEP-PG-molecules were characterized by having in plasma substantially low antithrombin-binding activities, this is not true for all the heparin-like compounds of the present invention. However, the capability of substantially complete inhibition of collagen-induced platelet aggregation, which is a cause of arterial thrombosis associated with vascular or microvascular injury and interventions should be present in all heparin-like compounds of the present invention, but in some of them said property is combined with potent antithrombin III accelerating activities. Said combined effect gives an additional advantageous property to the product, i.e. to the compounds, preparations and devices of the present invention.

Thus, the terms "heparin or heparin-like glycosaminoglycan" and "heparin or heparin-like proteoglycan" in the present invention means not only mast cell-derivable heparin proteoglycans (HEP-PG) or heparin glycosaminoglycans (HEP-GAG), but also include heparin-like glycosaminoglycans and heparin-like proteoglycans, which are produced synthetically, semisynthetically or using recombinant DNA techniques.

In its broadest aspect the term "heparin-like compounds" means linear or branched heparin-like glycosaminoglycans, i.e. compounds composed of hundreds of monosaccharides comprising amino-groups and being connected or covalently attached to natural or synthetic or semisynthetic core molecules.

Such heparin-like compounds are obtainable from naturally occurring glycosaminoglycan species such as chondriotin sulphates, keratan sulphates, dermatan sulphates, heparan sulphates and/or hyaluronic acid, either as such or modified by chemical or biotechnological means, including recombinant-DNA-techniques to provide molecules, which fulfill the requirements and prerequisites set out above and which are characteristic features of the native mast cell-derivable heparin proteoglycans (HEP-PG) and heparin glycosaminoglycans (HEP-GAG). It is not necessary to isolate the heparin-like glycosaminoglycan molecules from nature. They can be also synthesized or fragments of naturally occurring species can be coupled together especially with heparin-fragments to provide new variants, the properties of which can easily be tested by known methods by those skilled in the art.

The term "mast cell" means mast cells related to connective tissue, such as vascular or serosal mast cells of mammalian or human origin, which can be isolated from respective tissues and which cells can be cultivated in a culture medium under conditions, which allow proliferation of the cells and secretion of the heparin proteoglycans (HEP-PG) of the present invention upon lysis and/or activation of the-mast cells. Mammalian mast cells, including human mast cells, are available and described in literature (Butterfield J H, Weiler D, Dewald G, Gleich G J, Leuk Res 1988; 12: 345-55; Nilsson G, Blom T, Kusche-Gullberg M, Kjellen L, Butterfield J H, Sundstöm G, Nilsson K, Hellman L. Scand J Immunol 1994; 39:489-98). The mast cells can be genetically modified, by conventional mutagenesis or recombinant DNA techniques.

The term "coupling density" means that negatively charged heparin or heparin-like glycosaminoglycans can be spatially brought together in such a way that the characteristic features of the heparin-like compounds of the present invention are obtainable. This is achieved either by preparing multiplied heparin or heparin-like glycosaminoglycans or by bringing shorter molecules together in a spatial configuration, which allows a sufficient concentration and optimal presentation of negative charges.

The term "spacer/linker molecules" means polymeric compounds provided with a multitude of groups which allow binding of the desired compounds or molecules to the core molecule. SPSD is one example, but those skilled in e.g. protein chemistry and combinatorial chemistry, can find a multitude of other equally advantageous spacer/linker molecules.

The term "capacity of substantially complete inhibition of platelet aggregation on collagen in flowing whole blood" means that the interaction between platelets and collagen can be prevented as measured by the methods set forth in Lassila R, Lindstedt K, Kovanen P T. Arteriosclerosis, Thrombosis, and Vascular Biology 1997; 17 (12): 3578-3587.

The term "local administration" or "local use" means that the heparin-like compounds of the present invention are administered to the injured region of the blood vessel as such or in the form of in situ or on place, i.e. locally or topically applicable preparations or compositions and/or as means or devices. The local administration is performed for example by flushing the exposed vascular tissue with the solution. The heparin-like compounds of the present invention can be used for coating devices, which are placed in contact with the injured blood vessels. Such devices are for example "coated stents" i.e. small devices, which are placed into the blood vessels to keep them open or "vascular grafts" which are used to replace weakened vascular tissues. Other examples of devices, which can be coated are for example extracorporeal circulation systems, the inner walls of which can be coated with the heparin-like compounds of the present invention.

The term "prophylactic treatment" means prevention of thrombosis in association with vascular or microvascular injuries and interventions by local or topical application, e.g. by flushing of the exposed vascular tissue with the heparin-like compounds of the present invention as such or as suitable preparations or in form of devices coated with said heparin-like compounds. The local administration of the heparin-like compounds can be used as such or in combination with systemic administration of conventional preparations.

The term "arterial thrombosis" means thrombosis in arteries in association with endogenous conditions, including atherotrombosis, and other hemostatic conditions in vasculature, vascular injuries and iatrogenic angioplasty and other interventions.

The term "preparation" means the heparin-like compounds of the present invention used in combination with compatible, pharmaceutically acceptable adjuvants, carriers in preparations, means and/or devices for administration to the patient.

The General Description of the Invention

The primary aim of the present invention was to compare the effects of the HEP-GAG- or HEP-PG-molecules of the present invention and standard heparins (average MWs of 15 and 5 kDa) on platelet-collagen interaction in vitro. In contrast to standard heparins, mast cell-derived HEP-PG- and HEP-GAG-molecules were shown to completely inhibit collagen-induced platelet aggregation and serotonin release in platelet-rich plasma. The inhibition caused by mast cell-derived HEP-GAG- and/or HEP-PG-molecules of the present invention was shown to be dependent on their macromolecular structure. In flowing blood, mast cell-derived HEP-GAG- and HEP-PG-molecules also inhibited platelet deposition on a collagen-coated surface both at low and high shear rates. Although, the mast cell-derived HEP- GAG- and HEP-PG-molecules did not block glycoprotein (GP) Ia/IIa-mediated platelet adhesion, they attenuated subsequent platelet activation and aggregation, as well as fibrinogen binding to platelets after collagen stimulation. The mast cell-derived HEP-GAG- and HEP-PG-molecules did not bind to platelets, but were tightly bound to von Willebrand Factor (vWf) enhancing its binding to collagen. While platelet adhesion at high shear rate and vWf binding to GP Ib after ristocetin stimulation was not markedly affected, the HEP-GAG- and HEP-PG-molecules of the present invention reduced thrombin-induced aggregation and vWf binding to GP IIb/IIIa. These findings implied that activation of vascular mast cells with ensuing secretion of HEP-PG may locally attenuate the thrombogenicity of matrix collagen by inhibiting its platelet-activating capacity.

To study the ability of the mast cell-derived HEP-PG to inhibit thrombin activity was the first objective of the study. Particularly, the inhibitory effect of the very high-molecular-weight heparin species was compared with the well-known anticoagulative function of standard heparins, which essentially relies on the potentiation of antithrombin III activity (Nader H B, Dietrich C P., in Lane D A and Lindahl U (eds): Heparin: Chemical and Biological Properties, Clinical Application. Erward Arnold, London. 1989, pp 81-96). The assays focusing on the differential capacities of HEP-PG, HMWH, and LMWH to inhibit thrombin (FIG. 1) showed that, in the absence of plasma proteins, HEP-PG had a better functional ability than HMWH to potentiate antithrombin III directly, whereas in the presence of plasma, HEP-PG were less potent than HMWH. These data could be understood if HEP-PG was, more effectively than HMWH, bound to plasma proteins, such as vWf, which were believed to compete with antithrombin III for binding to heparin. It has been shown that the greater the molecular weight of the heparin, the higher is its affinity for plasma proteins (Baruch D, Ajzenberg N, Denis C, Legendre J-C, Lormeau J-C, Meyer D. Thromb Haemost 1994; 71: 141-146; Young E, Prins M, Levine M N, Hirsh J. Thromb Haemost 1992; 67: 639-643). In all, it was concluded that the inhibitory potential of HEP-PG upon the observed platelet-collagen interaction (see Examples 15-16 below), as compared with HMWH and LMWH, could not be due to antithrombin III-dependent thrombin inhibition.

Figure 2:
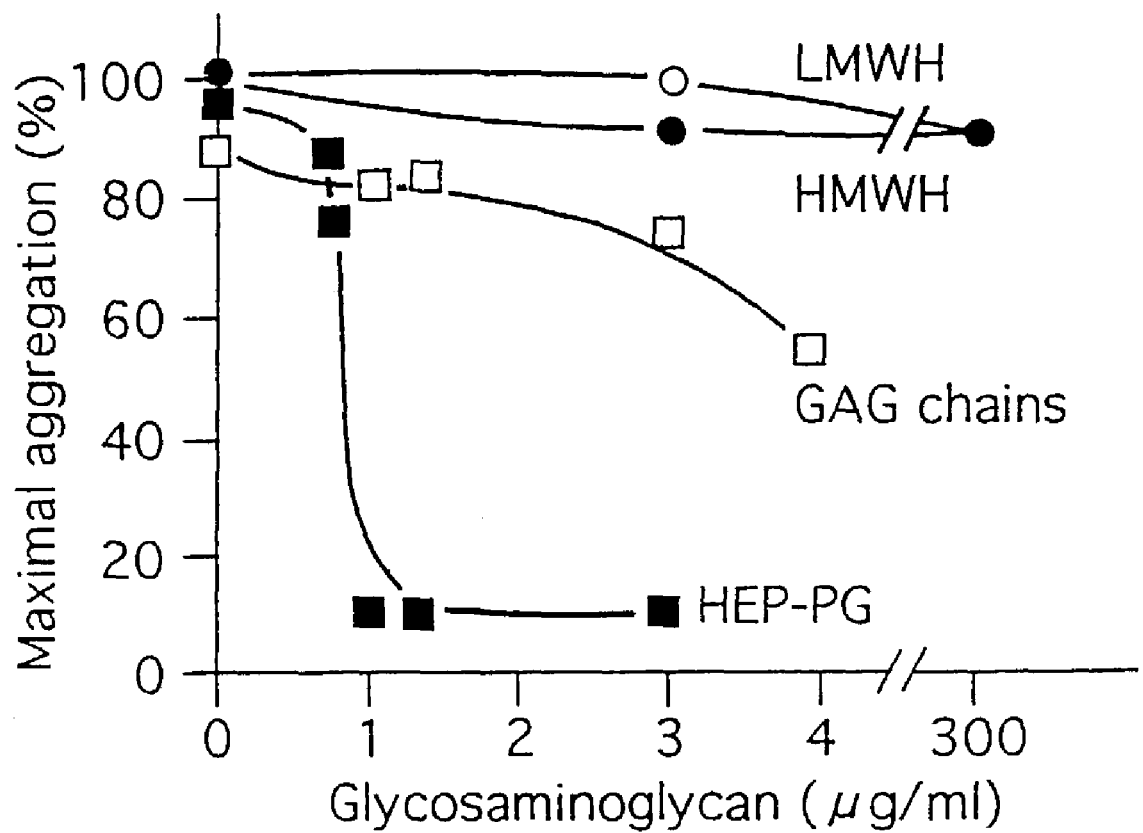
FIG. 2 shows comparative effects of mast cell-derived HEP-PG (MW 750 kDa), the heparin glycosaminoglycan (HEP-GAG) chains derived from HEP-PG (MW 75 kDa), HMWH (MW 15 kDa), and LMWH (MW 5 kDa) on collagen-(Sigma, collagen of the aggregation kit) induced platelet aggregation (25 µg/ml) maximal aggregation (%) in platelet rich plasma (PRP) anticoagulated with citrate.

The major findings of the present study were the total inhibition by HEP-PG of (i) collagen-induced platelet aggregation (FIG. 2), (ii) subsequent dense granule release (serotonin), and (iii) platelet deposition on immobilized collagen in flowing whole blood under both low and high shear rate conditions (FIG. 3). Previously, HMWH. (at concentrations >6 µg/ml) had been shown to impair platelet aggregation induced with a low-dose collagen in cation-depleted PRP (Fernandez F, N'guyen P, van Ryn J, Ofosu F A, Hirsh J, Buchanan M R. Thromb Res. 1986; 43: 491-495). In the present studies, it was found that mast cell-derived HEP-PG, in contrast to HMWH, totally inhibited collagen-induced platelet aggregation and serotonin release, irrespective of collagen concentration. Curiously, HEP-PG-molecules were shown to be able to prevent the action of collagen on platelets even when added to the platelet-rich plasma (PRP) 10 s after collagen. Mast cell-derived HEP-PG-molecules were shown to inhibit platelet aggregation by collagen more effectively in citrate-PRP than in PPACK-PRP, indicating that HEP-PG-molecules were most potent in blocking the cation-dependent platelet functions upon collagen stimulation (FIGS. 2, 3, 4). It was shown that the heterogeneity of platelet GP Ia/IIa resulted in variability of platelet responses among individuals and this was probably reflected in the somewhat variable inhibitory effect of HEP-PG on the aggregation of the gel-filtered platelets. The results were shown to be to be related to the multiple structure of the heparin glycosaminoglycan (HEP-GAG) molecules.

Since, under the conditions used, HEP-PG-molecules appeared not to bind directly to collagen or to resting platelets, HEP-PG-molecules disturbed platelet-collagen interaction through other mechanisms. The finding that although HEP-PG did not inhibit $Mg^{2+}$-dependent platelet adhesion, they did impair the subsequent platelet aggregation (FIGS. 4 and 5), implied attenuated transmission of the activation signal from GP Ia/IIa to GP IIb/IIIa. Thus, the detected decrease in fibrinogen binding was secondary to the impairment of collagen-induced platelet activation. The suggestion that HEP-PG did not directly interfere with GP IIb/IIIa was supported further by normal ADP- and epinephrine-induced aggregation and fibrinogen binding in the presence of HEP-PG. Similar results were obtainable with HEP-GAG molecules of the present invention.

The present findings implied an impairment of activation which follows adhesion of the platelets on collagen (FIGS. 3, 4, 5), leading to inhibited platelet recruitment in flowing blood at both low and high shear rates. Since HEP-PG did not attenuate $Mg^{2+}$-dependent platelet adhesion, direct inhibition of GP Ia/IIa as the underlying mechanism could be excluded. HEP-PG-molecules, being macromolecules with a strong negative charge, which inhibited not only collagen- but also thrombin-induced aggregation, could have disrupted the outward movement of negatively charged platelet membrane phospholipids during activation with agonists (Bevers E M, Comfurius P, Zwaal R F A. Blood Rev 1991; 5: 146-154). After GP Ia/IIIa-mediated adhesion to collagen the subsequent decrease in platelet function could have been mediated by the reduced ligand binding to GP IIb/IIIa. Indeed, HEP-PG decreased fibrinogen binding to collagen-stimulated platelets and HEP-GAG was shown to do the same. Under flow conditions, platelet recruitment to collagen depends crucially on vWf, and its binding to platelet GP Ib and IIb/IIIa, as well as to collagen. GP IIb/IIIa could be triggered by thrombin to bind vWf, and under conditions when hirudin is used to freeze thrombins proteolytic actions 60 s after challenging platelets. HEP-PG also reduced the binding of vWf to platelets (See Table II below). In summary, after platelet adhesion to collagen, HEP-PG blocked platelet activation and also, by binding tightly to vWf, reduced its availability to GP IIb/IIIa. The mast cell-derived HEP-GAG- and HEP-PG-molecules, by binding to vWf can also result in disturbed interaction of vWf not only with GP IIb/IIIa, but also with GP Ib. Thus, ristocetin-induced platelet aggregation was markedly reduced by HEP-PG (See Table I below).

At the concentration of HEP-PG used, the vWf binding to platelets stimulated with ristocetin (static conditions) was not affected, although 100-fold excess of HMWH did inhibit the vWf binding. In blood flowing at high shear rates, in which HEP-PG inhibited platelet-collagen interaction, these macromolecules could certainly have a more potent effect on vWf-dependent platelet activation than in the static binding assays. Indeed, HMWH has previously been reported to severely impair vWf-dependent platelet functions both in vitro and in vivo (Sobel M, McNeill P M, Carlson P L, Kermode J C, Adelman B, Conroy R, Marques D:, J Clin Invest 1991; 87: 1787-1793). However, HEP-PG enhanced, rather than inhibited the binding of vWf to collagen, which is mediated also by other domains of the vWf molecule than the A1 domain, where the GP Ib and heparin binding areas are located. The enhanced binding of vWf to collagen is assumed to have sealed the platelet-activating domains of collagen.

Mast cells, one of the sources of the heparin-like molecules of the present invention, are prevalent in the adventitial layer of vessel walls and in the perivascular areas of venules (Galli S J. N Engl J Med 1993, 328: 257-265). They are also present in the arterial intima, the site of atherogenesis and activated mast cells have been found to infiltrate into the inflammatory shoulder regions of coronary atheromas, the most common site of rupture (Kovanen PT, Kaartinen M, Paavonen T. Circulation 1995; 92: 1084-1088). Upon activation, such as occurs during inflammation, mast cells degranulate and exocytose an array of potent vasoactive mediators, of which the short-lived leukotrienes and prostaglandins, platelet-activating factor, and histamine are known to stimulate platelets. Histamine releases endothelial von Willebrand factor (vWf) and P-selectin, two factors that are important adhesive signals to platelets and leukocytes (Wagner D D. Thromb Haemost 1993; 70: 105-110). Furthermore, mast cells secrete glycosaminoglycans, from which the clinically used heparins are derived (Nader H B, Dietrich C P., in Lane D A and Lindahl U (eds): Heparin:Chemical and Biological Properties, Clinical Application. Erward Arnold, London. 1989, pp 81-96), whereas activated platelets secrete platelet factor 4, a heparin-neutralizing factor, and heparitinase, a heparin-cleaving endoglycosidase. Thus, there appears to be an interplay between these two cell types after their activation, which has been, however, poorly characterized so far.

Whether mast cell activation was involved in hemostasis could be evaluated during anaphylaxis and in mastocytosis, two clinical conditions in which mast cells become excessively activated. Yet in these conditions, thrombosis was not prevalent despite the release of platelet agonists and potent inflammatory mediators which caused changes in vascular endothelium, i.e. downregulation of its nonthrombogenic properties, induction of adhesive molecules, increased permeability and even exposure of subendothelial structures (Wagner D D. Thromb Haemost 1993; 70: 105-110).

It therefore seemed likely, that activated mast cells were also able to counteract their own thrombogenicity. Previously, in addition to their anticoagulant potential, the clinically useful high-molecular-weight heparin glycosaminoglycans (HMWH; average MW 15 kDa) had been shown to inhibit the platelet aggregation induced by low-dose collagen (Fernandez F, N'guyen P, van Ryn J, Ofosu F A, Hirsh J, Buchanan M R. Thromb Res. 1986; 43: 491-495); interestingly, this inhibitory effect of heparin was found to be directly related to the molecular weight of the heparins used.

In the studies leading to the present invention, the HEP-GAG- and HEP-PG-molecules were released from mast cell granules after their exocytosis. The residual proteoglycans that form the insoluble matrix of the granules after release of the soluble HEP-PG (the granule remnants; diameter 0.5-1.0 µm) were composed solely of heparin glycosaminoglycan chains (Lindstedt K, Kokkonen J O, Kovanen P T. J Lipid Res 1992; 33: 65-74). On the other hand, the soluble proteoglycans released from the granules into the extracellular fluid contained heparin and to a small extent also chondroitin sulphate glycosaminoglycan chains (Lindstedt K, Kokkonen J O, Kovanen P T. J Lipid Res 1992; 33: 65-74). The differential effects of heparinase and chondroitinase treatment on the soluble HEP-PG, the former decreasing their inhibitory activity and the latter not, revealed that the inhibitory effects on platelet-collagen interaction were due to the heparin glycosaminoglycan component of the HEP-PG. In structural analysis of the soluble HEP-PG the composition of disaccharide units is typical of heparin (J-p.Li, P. Kovanen, U. Lindahl, unpublished results). Therefore, it could be concluded that the observed functional differences between HEP-PG and commercial heparins depended on other factors than the composition of the glycosaminoglycan chains. Thus, the ability of intact HEP-PG (MW 750 kDa) to inhibit platelet function was greater than that of the heparin glycosaminoglycan chains (MW 75 kDa) released from HEP-PG, which, again, was greater than that of HMWH (MW 15 kDa) or LMWH (MW 5 kDa) (FIG. 2). Taken together, the above findings indicated that both the large size of the heparin chains and their attachment to a core protein to create high molecular weight heparin proteoglycans (HEP-PG) of the present invention were the most important factors contributing to the observed inhibition.

The inhibitory potential of mast cell-derived HEP-PG was related to the heparin chains only, since destroying this moiety with heparinase eliminated the inhibitory potential. After the HEP-PG was treated with high salt concentrations to detach the ion-mediated binding of proteases, i.e. chymase, tryptase and carboxypeptidase A attached to the glycosaminoglycan chains, the described inhibitory capacity against collagen-induced platelet aggregation was present.

Protamine sulphate, known to neutralize the negative charge of the standard heparin at equimolar concentrations prevented the effect of HEP-PG only at a 100-fold molar excess. This could indicate that platelet-derived factor 4 which is the natural antagonist of heparin and is released during platelet activation, would be needed in extremely high local concentrations to neutralize HEP-PG. HEP-PG retained the inhibitory potential even in the presence of platelet agglutinating concentrations of polylysine having the molecular weight of 500 000. All this evidence indicated that the strong negative charge of the heparin chains is crucial for the activity of HEP-PG.

Platelets interacting with collagen exposed by vascular injury are believed to play a crucial role in both hemostasis and atherothrombosis. The importance of vascular collagen in platelet-vessel wall interactions is clear in patients with bleeding disorders in whom collagen synthesis is defective, by platelet defects of glycoprotein receptors for collagen or mabs against GP Ia/IIa, and by the enhanced thrombogenicity of smooth muscle cell matrix when collagen synthesis is optimized. Mast cell-derived HEP-PG could be secreted locally into the subendothelium and adventitia where mast cells were present and where they could be activated by various stimuli (Kolodgie F D, Virmani R, Cornhill J F, Herderick E E, Smialek J. J Am Coll Cardiol 1991; 17: 1553-1560). The significant inhibitory capacity of HEP-PG in platelet reactivity towards collagen, implied a novel mast cell-dependent physiological mechanism limiting thrombosis in the vascular wall. The mechanism was believed to depend upon the multiple structure of the heparin glycosaminoglycan (HEP-GAG) molecules. The initial findings were later confirmed and could be found also in other heparin-like compounds.

Another aim of the present study was to assess the effects of mast cell-derived heparin proteoglycans (HEP-PG) on platelet-collagen interactions. A model with rat serosal mast cells was used. These cells are filled with cytoplasmic secretory granules composed of HEP-PG with a molecular weight of 750 kDa (range 750 to 1000 kDa), each monomer containing, on average, ten heparin glycosaminoglycan chains with a molecular weight of 75 kDa (range 50 to 100 kDa) (Yurt R W, Wesley Leid, Jr. R, Austen K F. J Biol Chem 1977; 252: 518-521; Lindstedt K, Kokkonen J O, Kovanen P T. J Lipid Res 1992; 33: 65-74).

Upon activation, mast cells expelled some of their granules into the extracellular fluid where a fraction of the granule HEP-PG became solubilized (Lindstedt K, Kokkonen J O, Kovanen P T. J Lipid Res 1992; 33: 65-74). It was found that these soluble HEP-PG strongly inhibited collagen-induced platelet aggregation and platelet interaction with immobilized collagen. The findings implied that heparin proteoglycans (HEP-PG) containing multiple heparin glycosaminoglycans (HEP-GAG) or HEP-GAG-molecules as such attenuated the reactivity of platelets to the vascular extracellular matrix, thereby counteracting the other, potentially thrombogenic effects of mast cells. The multiple character of the HEP-GAG-molecular structure was shown to be very important to achieve the desired effect and in the present invention it has been shown that the activity of mast cell-derived HEP-GAG-molecules as well as of other heparin-like compounds is based on a molecular multiplicity and/or high coupling density of negatively charged heparin or heparin-like glycosaminoglycans.

The improvement obtained by the heparin-like compounds of the present invention, especially the mast cell-derived HEP-GAG- and HEP-PG-molecules, was shown to be based on the fact, that it completely inhibits collagen-induced platelet aggregation and serotonin release in platelet-rich plasma. Furthermore, the heparin-like compounds of the present invention should preferably inhibit platelet deposition on collagen-coated surfaces in flowing whole blood both at low and high shear rates. In the same way as the mast cell-derived multiple HEP-GAG- and HEP-PG molecules, they should preferably attenuate platelet activation and aggregation as well as fibrinogen binding to platelets after collagen stimulation, simultaneously by strongly binding to von Willebrand factor (vWf) and enhancing its binding to collagen, likely sealing some crucial platelet-activating domains of collagen. The heparin-like compounds should preferably also reduce thrombin-induced aggregation and subsequent binding of von Willebrand factor to glycoprotein GPIIb/GPIIIa-complex. Inhibition of collagen-induced platelet aggregation in platelet suspension and platelet interaction with immobilized collagen in flowing whole blood should be their most prominent property.

The fact that allergen-induced mast cell activation has been shown to significantly prolong bleeding time and diminishing thrombin generation in bleeding time blood in volunteers (Kauhanen P, Kovanen P T, Reunala T, Lassila R. Thromb Haemost, Thromb Haemost 1998; 79:843-7) likely explain skin mast cell activation-induced prolongation of bleeding time by the attenuated reactivity of platelets to vascular extracellular matrix as a property of mast cell-derived heparin. proteoglycans (HEP-PG) and multiple heparin glycosaminoglycans (HEP-GAG).

Mast cell-derived HEP-PG was shown to abolish thrombus formation on rat femoral arteries during anastomosis in an acute model lasting 10 min and a follow-up model of 72 hours—a desired property of the heparin-like compounds of the, present invention. It was shown that the improvements obtained especially with HEP-GAG- and HEP-PG-molecules are obtainable also with some other heparin-like compounds of the present invention having the defined technical features and consequently it was believed that the improvements including platelet aggregation inhibition in connection with vascular or microvascular injuries and other severe disorders in the vascular system caused by e.g. thrombosis could be obtained with other heparin-like compounds of the present invention. The heparin-like compounds of the present invention, including the mast cell-derived HEP-GAG- and HEP-PG-molecules were shown to offer locally more efficient prophylactic treatment and prevention of disorders than unfractionated heparin, in which there was undesired or excessive blood clotting and e.g. post-operative healing. It was shown that heparin-like compounds of the present invention like mast cell-derived heparin proteoglycans (HEP-PG) containing multiple heparin glycosaminoglycan (HEP-GAG) moieties were responsible for the effect of attenuating the reactivity of platelets to vascular extracellular matrix. It was shown that it was the multiple structure of the HEP-GAG-moieties of the mast cell-derived HEP-PG-molecules or a high coupling density of negatively charged glycosaminoglycan units, that provide the heparin-like compounds of the present invention that provided them with their unique properties. Thus, it was shown that a spheroidal, bottle-brush-like spatial presentation or configuration is of special importance for obtaining the desired effects and consequently, it could be shown that synthetic or semisynthetic HEP-GAG-molecules with multiple end-to-end- and/or end-to-side-coupled glycosaminoglycan units as such are especially advantageous and characterized by the same or improved properties as compared to the mast cell-derived HEP-GAG- and HEP-PG-molecules.

The other heparin-like compounds of the present invention were produced by coupling glycosaminoglycan units, preferably heparin glycosaminoglycan units end-to-end or end-to-side to form sufficiently large glycosaminoglycan molecules, and said multiple straight-chained or branched glycosaminoglycan molecules could be used as such or conjugated to a natural, synthetic or semisynthetic core molecule, such as a globular protein or a polypeptide chain, preferably a short polypeptide chain and their properties were easy to screen and test.

The heparin-like compounds of the present invention can, after being found active, be used in prophylactic treatment of arterial thrombosis associated with vascular or microvascular injuries and interventions.

The heparin-like compounds of the present invention are useful for the manufacturing of preparations for local use as well as for coating devices, such as stents, grafts and/or extracorporeal circulation systems. Said preparations, means and devices can subsequently be used in prophylactic treatment of arterial thrombosis associated with vascular injuries and interventions as well as for prevention of interactions with of flowing whole blood with collagen. Thus, the heparin-like compounds of the present invention are used to manufacture pharmaceutical preparations or medicaments for improved, i.e. more efficient local treatment to prevent thrombosis, including atherotrombosis and other hemostatic conditions including vascular injuries and other changes in vascular endothelium with improved efficiency.

The heparin-like compounds of the present invention are above all used in prophylactic treatment of arterial thrombosis associated with vascular or microvascular injuries and interventions and they are locally applied or administered as such or in combination with suitable, compatible adjuvants, carriers, etc. or as devices, such as stents, grafts, etc., which have been coated with the heparin-like compounds of the present invention.

Different types of medicinal devices, such as stents, their use and their coatings have been extensively discussed and are described e.g. in the following patent publications, the contents of which are herewith incorporated into this specification:

WO 98/22162, EP 832618, U.S. Pat. No. 5,718,862, U.S. Pat. No. 5,603,722, U.S. Pat. No. 5,583,213, U.S. Pat. No. 5,571,166, U.S. Pat. No. 5,554,182, U.S. Pat. No. 5,618,298, U.S. Pat. No. 5,342,621, U.S. Pat. No. 5,409,696.

Said devices are also commercially available in a multitude of different forms suitable for different applications. Such products are e.g. Microstent II™ products from AVE (Arterial Vascular Engineering, Santa Rosa, Calif. 95403, USA), NIR™ and NIROYAL™ stents from SciMed Boston Scientific Corporation, France. The devices are rigid, semirigid, elastic helixes generally made of plastics, silicons, metals, materials of hydroxylapatit. A specially preferred material for preparations of stents is polylactic acid but other substances with the desired flexible, elastic, semirigid or rigid consistence capable of being coated with the HEP-GAG- and/or HEP-PG-molecules of the present inventions are in no way excluded from the scope of the present invention.

The invention is also related to preparations with pharmaceutical or medicinal activity for use in prophylactic treatment and/or prevention of thrombosis, including thrombosis associated with vascular injuries, such as angioplasty, stent and/or graft application including other vascular or microvascular surgery.

The methods and materials used to provide the water-soluble, heparin-like compounds of the present invention as well as preparations and devices containing them and their use are discussed in more detail in the examples below.

The examples are only illustrative and should not be interpreted as limiting the scope of the invention. One skilled in the art will immediately recognise the further possibilities to apply this invention.

EXAMPLES DESCRIBING THE METHODS AND MATERIALS USED

Example 1A

Methods of Obtaining Heparin Proteoglycan (HEP-PG) Heparin Proteoglycans (HEP-PG) Exocytosed by Stimulated Mast Cells Mast cells were isolated from rat peritoneal and pleural cavities as described (Yurt R W, Wesley Leid, Jr.R, Austen K F. J Biol Chem 1977; 252: 518-521). In a standard assay, 10-13×10$^6$ mast cells were incubated in 1 ml of PBS buffer containing 0.1 mg/ml HSA (Red Cross Transfusion Service, Helsinki, Finland) and 5.6 mM glucose. After preincubation (15 min, 37° C.) the cells were incubated for 15 min with compound 48/80 (Sigma Chemical Co) (5 µg/ml), a specific mast cell agonist, to induce mast cell degranulation. Control experiments showed that compound 48/80 does not induce platelet aggregation. The degranulated mast cells were then sedimented by centrifugation at 150×g for 10 min, the supernatant was centrifuged for a further 15 min at 12 000 g to sediment the exocytosed granules, and the granule-free supernatant was analyzed for its content of Alcian Blue-reactive (Fluka) material (Lindstedt K, Kokkonen J O, Kovanen P T. J Lipid Res 1992; 33: 65-74). In the experiments performed in the absence of plasma, soybean trypsin inhibitor (Sigma) was included to inactivate mast cell-derived neutral serine proteases. Throughout the experiments, HEP-PG were compared with up to 300-fold concentrations (measured as Alcian Blue-reactive material) of commercial porcine unfractionated, high-molecular-weight heparin (HMWH) (Leiras, Finland) (average MW 15 kDa, 1% <7.5 kDa, 1 mg=100 IU USP) and fractionated low-molecular-weight heparin (LMWH) (Fragmin, Kabi Pharmacia) (average MW 5 kDa, 25% >7,5 kDa, 1 mg=152 anti Xa units). HEP-PG did not alter the content of ionized calcium or magnesium in the buffers or plasma (Microlyte 6, Kone Instruments, Finland) (Boink A B T J, Buckely B M, Christiansen T F, Covington A K, Müller-Plathe D, Sachs Ch, Siggaard-Andersen O. Eur J Clin Chem Clin Biochem 1991; 29: 767-772). HEP-PG were radiolabeled by incubating mast cells with sodium $^{35}$S-sulphate (Amersham International), as described (Lindstedt K, Kokkonen J O, Kovanen P T. J Lipid Res 1992; 33: 65-74). In some experiments HEP-PG were treated with chondroitinase ABC and heparinase (both from Seikagaku Kogyo Co).

Example 1B

Methods of Obtaining Heparin Proteoglycan (HEP-PG) Natural Heparin Proteoglycans (HEP-PG)

Connective-type mast cells, such as skin and serosal mast cells of mammalian origin can be isolated with the method described in example 1A or slightly modified methods, not only from rats, but also from other mammalian species such as bovine, swine, sheep, etc. During slaughtering of cows or pigs peritoneal; and pleural lavage is performed with phosphate buffered saline. The pooled fluids are centrifuged once at 100×g for 5 min and the sedimented cells are resuspended in PBS. The isolation of mast cells is obtained by gradient centrifugation in Ficoll, during which mast cells concentrate at the interphase between 30% and 40% Ficoll layer. To obtain the soluble proteoglycans mast cells are stimulated with compound 48/80, a basic polyamine, or calcium ionophore A 23187, which induce exocytosis of the mast cell granules.

In contrast to the traditionally isolated bovine or swine-derived heparin glycosaminoglycans, which are degraded by endoglycosidases, cultured purified mast cells accumulate free, essentially undegraded polysaccharide chains, which do not undergo endoglycosidic cleavage (Nader H B, Dietrich C P., in Lane D A and Lindahl U (eds): Heparin: Chemical and Biological Properties, Clinical Application. Erward Arnold, London. 1989, pp 81-96). Lymphnode-derived mast cells can be cultured, as well as HMC-1, a human cell line. These cultured cells can be genetically engineered to enhance the production of HEP-PG. Co-cultivation of murine bone marrow-derived mast cells with fibroblasts has been reported to increase biosynthesis of heparin relative to chondroitin sulphate. The use of co-cultivation is recommended in order to improve proliferation of cells with subsequent release of HEP-PG-molecules.

Such heparin proteoglycans (HEP-PG) are known to be typically more resistant to proteolytic degradation, likely due to the high degree of substitution of the peptide core with carbohydrates. This increases the potential use of the HEP-PG molecules because of their capacity for prolonged activity and due to their increased stability and storability or shelf-life.

Example 1C

Methods of Obtaining Human-derived Natural Heparin Proteoglycan (HEP-PG) from Human Mast Cells Connective-type mast cells, such as skin and serosal mast cells of human origin can be isolated with the method described in Example 1A or slightly modified methods. It is to be observed that only a small sample is required, which can be obtained from a patient with routinely performed biopsy procedures. The human derived mast cells are thereafter cultivated in a conventional cell culture media and under conditions allowing good proliferation of the mast cells., The mast cells are harvested with phosphate-buffered saline and treated as described in Example 1A and 1B. It is also to be observed that once cultured, the cell cultivate can be preserved and stored by per se known methods; and provides an unlimited source for producing more cells.

Example 1D

Methods of Obtaining Heparin Proteoglycan (HEP-PG) Synthetic High-molecular Weight Heparin Chains and HEP-PG The multiple structure of the HEP-GAG- and HEP-PG- molecules is essential for the inhibitory action upon platelet-collagen interaction. However, also the very long glycosaminoglycan (HEP-GAG) chains, of 75±25 kDa or more, retain the inhibitory potential, in contrast to the lower molecular weight species. Thus, the synthetic chains should contain at least 3-10 heparin glycosaminoglycan units with a molecular weight of at least 12 but preferably 15-20 kDa, coupled end-to-end or end-to-side to each other to form straight or branched heparin glycosaminoglycan chain molecules. To obtain a more native-like construct these separate long heparin (HEP-GAG) chains could also be coupled to a polymeric linker molecule, as described in the U.S. Pat. No. 5,529,958. Useful polymeric core molecules are for example chain-like peptides comprising repeated Ser-Gly-sequences or globular proteins such as albumin (HSA), which can be coupled to heparin by the aid of linker molecules such as SPDP, N-succinylimidyl-3-(2-pyridylthio) propionate.

An overdose of heparin to the amount of linker should be used. But naturally the proportions can vary depending upon the desired structure of the synthesized heparin-like compound. These both options, i.e single heparin HEP-GAG- molecules and the synthetic HEP-PG constructs provide possibilities to prepare improved preparations with less antigenic properties because the potentially antigenic protein part of natural heparin proteoglycans (HEP-PG) is missing. Alternatively to the high molecular weight multiple HEP-GAG molecules optimal heparin densities can be obtained by coupling standard unfractionated heparin (12 kDa) chains on globular core molecules, such as albumin by means of SPSD, a heterobifunctional coupling reagent.

Example 1E

Heparin Cross-linking to Bovine Serum Albumin (BSA)

Heparin (Lövens, MW 15 kD) 2 mg was diluted in PBS and coupled to heterobifunctional coupling reagent SPDP (N-succinimidyl-3-(2-pyridylthio)-propionate, Fluka Chemie AG, Switzerland) 1 mg in methanol. The heparin-coupling reagent solution (200 µl) was activated by DTT (dithiothreitol, Sigma Chemicals Co) 10 mg/ml (800 µl), and the effect of DTT was monitored at 343 nm spectrophotometrically. The sample 1 ml was eluted through the PD-10 column (Pharmacia Biotech, Pharmacia Biotech AB, Uppsala, Sweden) and 10 fractions (1 ml each) were collected. The absorbance of the fractions was analyzed at 343 nm in spectrophotometrically and the four fractions not containing free DTT were pooled together.

BSA 0.250 mg (100 µl) and SPDP 0.5 mg (50 µl) were agitated for 20 min at 22° C. and 850 µl sodium chloride (0.9%) was added. The sample was eluted through PD-10 column and fractions of 1 ml were collected. The exclude unbound SPDP 100 µl of the fractions were treated with 900 µl of DTT and absorbance was measured at 343 nm. The five fractions not containing free SPDP were pooled. The sodium chloride content was raised up to 3M in the pooled fractions of both heparin-SPDP and BSA-SPDP, and these two pools were incubated together overnight at 4° C. to induce the coupling. The heparin-BSA coupled sample was eluted with 0.9% NaCl through Sephacryl S-300 gel (Pharmacia Biotech) (height 30 cm) or through PD-10. 0.5 ml fractions 1-45 or 1-25, respectively, were collected and basing on BSA-content, i.e. absorbance at 280 nm, fractions 24-36 or 16-21, respectively, were collected.

The fractions were concentrated, dialyzed for 30 min against aqua using VSWP02500 film (Millipore Corp, Bedford, Mass.) or minidialyzed (Spectrapor molecular porous membrane MWCO:12-14.000, Spectrum Medical Industries Inc. Laguna Hills, Calif.) for 30 min and repeatedly for 2 hours against aqua. Subsequently, fractions were analyzed for glycosaminoglycan content (Blyscan, Biocolor Ltd, Belfast, North Ireland) and tested in aggregometer (see FIG. 10). As an example the aggregation curve for PD-10 separated fraction #21 having 0.74 µg/ml heparin is given. All fractions 18-21 showed inhibitory capacity against collagen-induced platelet aggregation (for more details see Example 22).

Example 2

Inhibition of Thrombin

The relative potencies of HEP-PG, HMWH, and LMWH were measured with thrombin time in pooled citrated plasma and with a chromogenic assay using a thrombin substrate (S-2238, Chromogenix, Kabi Pharmacia) (Larsen M L, Abildgaard U, Teien A N, Gjesdal K. Thromb Res 1978; 13: 285-288). In the latter assay, 1 U/ml (110 U/mg) of thrombin (Dade, Baxter Healthcare Co, Fl.) was the selected dose after titrating the effects of the glycosaminoglycan concentrations used., Exogenous thrombin activity was assessed in the presence of antithrombin III (Kabi Pharmacia) alone and at two plasma dilutions (1:5 and 1:40 in Tris—NaCl-HSA, pH 8.2) as a control for the competitive binding of the glycosaminoglycans to plasma proteins. In the absence and presence of plasma (1:40 dilution), exogenous antithrombin III was used at two concentrations, 7.5 and 10 mU/ml. The reagents were applied to 96-well microtiter plates (Falcon 3072, Becton Dickinson) on ice, and incubated for 10 min at 37° C. S-2238 was added, the reaction was stopped with 20% acetic acid, and residual thrombin activity was assessed spectrophotometrically (405 nm) (Labsystems Multiscan MCC, Labsystems, Finland).

Example 3

Platelet Preparation

Blood for the studies was donated by healthy volunteers not using any medication. Nine volumes of free-flowing blood were collected via a PTFE cannula (Viggo, Sweden) into one volume of D-phenylalanyl-1-propyl-1-arginine chloromethyl ketone (PPACK) (Calbiochem) (200-400 µM) or acidic citrate dextrose anticoagulant (ACD) [pH 4.9 for aggregation (pH 7.3 in PRP) and pH 4.5 for gel filtration]. Platelet-rich plasma (PRP) was separated by centrifugation (180×g, 12 min, 22° C.) and used for platelet aggregation studies and adhesion assays. For detecting deposition of serotonin-positive platelets and release reaction, the platelets in PRP were labeled with $^{14}$C-serotonin (specific activity 8

μCi/ml, final concentration of serotonin 40 nM) (Amersham) or 3H-serotonin (specific activity 15 μCi/ml), final concentration of serotonin 10 nmol) (Amersham) for 15 min at 37° C. In blood perfusion studies, the labeled PRP was added to the remaining blood. The method of platelet detection by serotonin labeling has been previously validated with the determination of deposited protein and with electron microscopy (Mustonen P, Lassila R. Thromb Haemost 1996; 75: 175-181).

Gel-filtered platelets were prepared from PRP after a single washing step in the presence of $PGE_1$ (25 ng/ml) and apyrase (1U/ml) (both from Sigma) and the platelet suspension was then passed through a Sepharose CL-2B column (Pharmacia LKB). After gel filtration, ristocetin (1.0 mg/ml) (Sigma) did not induce a platelet response, indicating that vWf was lacking, and the cell suspension was also devoid of antithrombin III activity, as shown by crossed immunoelectrophoresis (Lane D A, Boisclair M D. in Thompson J M, (ed): Blood Coagulation and Haemostasis. A Practical Guide. Churchill-Livingstone. 1991, pp 45-70). Gel-filtered platelets were used for aggregation studies, for studying $Mg^{2+}$-dependent platelet adhesion to collagen, and for binding the ligands (fibrinogen and vWf) that mediate platelet-to-platelet interaction. The elution buffer was HEPES with 1 mM $Mg^{2+}$ (Timmons S, Hawiger J. in Hawiger J, (ed): Platelets:Receptors, Adhesion, Secretion. Methods in Enzymology. Academic Press, San Diego, Calif. 1989; 169, 11-22). Usually, 2 mM $Ca^{2+}$ was added to the suspension of gel-filtered platelets, but when assaying Mg-dependent (2 mM) adhesion, $Ca^{2+}$ was omitted (Santoro S A. Cell 1986; 46: 913-920). HSA (4%) solution with 2 mM $Ca^{2+}$ and 1 mM $Mg^{2+}$ was used when the platelet-collagen interaction was studied in flowing reconstituted blood without plasma factors (Sakariassen K J, Muggli R, Baumgartner H R. in Hawiger J (ed): Platelets: Receptors, Adhesion, Secretion. Methods in Enzymology. Academic Press, San Diego, Calif. 1989; 169: 37-70.) After centrifugations and reconstitutions, the final platelet suspension was allowed to stabilize for 30 min prior to the assays.

Example 4

Platelet Aggregation

Aggregation in PRP and in gel-filtered platelet suspension were studied with a Payton aggregometer (Payton Ass. Ltd, Canada). Pepsin-extracted collagen (Sigma, platelet aggregation kit), and fibrillar type I bovine collagen (Miller E J, Rhodes R K. Methods in Enzymology. 1982; 82: 33-64.), collagen reagent Horm (Nycomed, Hormon Chemie, Germany), thrombin, ristocetin, ADP (Sigma) and epinephrine (Bioanalytical Systems Inc., IN) were used as agonists, each added in a volume of 30 μl per 270 μl of platelet suspension. The effects of HEP-PG, HMWH, and LMWH were studied by adding them either during the 1-min preincubation or simultaneously with the agonist (collagen). In some instances, HEP-PG were added 10 and 20 s after the collagen. The response was assessed as the slope of primary aggregation (rate, 1/min) and as maximal aggregation (%).

Example 5

Immobilization of Isolated Fibrillar Collagen

Fibrillar collagen had been extracted from bovine achilles tendon by acetic acid extraction and salt precipitation without pepsin (Miller E J, Rhodes R K. Methods in Enzymology. 1982; 82:33-64). Collagen (at a concentration of 0.36 mg/ml) was kept in 0.5 M acetic acid and fibril formation induced by neutralizing with 60 mM TES buffer (1:1) and incubating at 35° C. for 90 min in humid atmosphere (Holmes D F, Capaldi M J, Chapman J A. Int J Biol Macromol 1986; 8: 161-166; Williams B R, Gelman R A, Poppke D C, Piez K A. J Biol Chem 1978; 253: 6578-6585). For adhesion studies, this fibrillar collagen solution was sprayed five times on ethanol-washed round (diameter 1.5 mm) Thermanox coverslips (NUNC). The successive sprayings of collagen suspension were made just before the droplets dried. Collagen settled as a homogeneous layer of fibril-containing droplets ranging from 50 to 200 μm with both diameters and interspaces, as assessed by scanning electron microscope (JEOL JSEM 820, Japan). The coverslips were kept in a humid atmosphere before use on the same day. For perfusion studies, collagen was immobilized, and native-type fibrils were allowed to be formed in situ in PTFE tubing (Optinova, Finland) by adding TES and incubating the stoppered tubing at 35° C. for 90 min. After incubation, the tubing was rinsed with PBS.

Example 6

Platelet Interaction with Collagen in PRP or in $Mg^{2+}$-Buffer

Platelet adhesion to immobilized collagen was studied both in PRP (PPACK) and in gel-filtered platelets in HEPES with 2 mM $Mg^{2+}$ (Santoro S A. Cell 1986; 46: 913-920). Collagen-coated Thermanox coverslips were placed on the bottom of the 24-well plates (NUNC) (precoated with 2% HSA) and 1 ml of $^{14}C$-serotonin-labeled PRP or of gel-filtered platelets with platelet counts adjusted to 100 or to $300 \times 10^6$/ml (Thrombocounter C, Coulter Electronics) was added. Before the assay, the $^{14}C$-scintillation activity in the platelet suspension and the release of serotonin into plasma were measured in tubes with imipramine-formaldehyde on ice (centrifuged at 9500×g for 2 min) (Holmsen H, Dangelmaier C A. Measurement of secretion of serotonin, in Hawiger J (ed): Platelets:Receptors, Adhesion, Secretion. Methods in Enzymology. Academic Press, San Diego, Calif. 1989; 169: 205-210).

After incubation for 30 min either at 22° C. without rotation (to study adhesion of $100 \times 10^6$ platelets/ml) or at 37° C. during rotation at 100 rpm (to study aggregation upon adherent platelets from PRP $300 \times 10^6$ platelets/ml), the coverslips were removed, rinsed three times in buffer, and subjected to scintillation counting. The number of platelets deposited on the collagen-coated coverslip was calculated from the number of platelets added and from their specific activity. The release of serotonin from the platelets to plasma was also measured as described, and it was constantly below 5%. To assess the role of GP IIb/IIIa under these conditions, PRP was preincubated (15 min, 37° C.) with a mAb against GP IIb/IIIa (m7E3, kind gift from Dr. Barry Coller) prior to the adhesion assay (Coller B S, Peerschke E I, Scudder L E, Sullivan C A. J Clin Invest 1983; 72: 325-338.

Example 7

Platelet Interaction with Collagen in Flowing Whole Blood or in Reconstituted Blood To study platelet interaction with collagen in PPACK-anticoagulated blood (30 ml) containing preincubated $^{14}C$-serotonin-labeled platelets, blood was recirculated for 5 min through the collagen-coated tubing, which was connected to a perfusion pump (Cole Parmer, Ill.). To induce different shear rates (200, 700 and 1700 1/s), at a flow rate of 10 ml/min, tubings of different diameters (1.1, 1.5 and 1.9 mm) were used. The collagen surface was stabilized by perfusing it with PBS (at 37° C. for 15 s) before the blood perfusion. After the perfusion the unattached platelets were rinsed off by perfusing with PBS for 30s. The adherent platelets were detached by incubating them in 2% SDS twice for 30 min and the lysates were subjected to scintillation counting. In some instances, scanning electronmicrographs were obtained from the surface after perfusion. Platelet counts, background radioactivity of the blood, and serotonin release were measured, as described for the adhesion assay. To study platelet-collagen interaction in the absence of plasma proteins, reconstituted blood with washed red cells, buffy coat, and gel-filtered $^{14}$C-serotonin-labeled platelets in HSA solution was used (Sakariassen K J, Muggli R, Baumgartner H R. in Hawiger J (ed): Platelets: Receptors, Adhesion, Secretion. Methods in Enzymology. Academic Press, San Diego, Calif. 1989; 169: 37-70.). We also immobilized standard heparin (at 10 mg/ml) and HEP-PG (10 pg/ml) to either fibrillar collagen (Horm) or to monomeric collagen obtained with pepsin from native acetic acid-extracted collagen type I described in the earlier perfusion experiments, where HEP-PG was used in solution.

Example 8

Interaction Between Platelets and HEP-PG

Binding of HEP-PG to resting platelets was assessed by incubating $^{35}$S-labeled HEP-PG with PRP or with gel-filtered platelets at 37° C. for 15 min. The $^{35}$S-scintillation activity was then recovered in plasma fractions and in platelets using sedimentation or gel filtration. HEP-PG were also immobilized on Thermanox coverslips by incubation for 30 min. The quantity of bound HEP-PG was determined from the $^{35}$S-binding, and it was 56±6 ng/cm$^2$ (mean±SD, n=4). Interaction of platelets with HEP-PG was then determined using the platelet adhesion assay, as described above.

Example 9

Binding of vWf and Fibrinogen to Activated Platelets vWf (specific activity 200 U/mg protein) (CRTS, France) (Burnouf-Radosevich M, Burnouf T. Vox Sang 1992; 62: 1-11) and fibrinogen were radioiodinated with I$^{125}$ (Amersham) by the method of Bolton & Hunter (Bolton A E, Hunter W M. Biochem J 1973; 133: 529-539). The structural stability of vWf and fibrinogen was confirmed by analysis with gradient (4-21%) SDS gel electrophoresis. The function of radiolabeled vWf was confirmed by ristocetin-induced aggregation of gel-filtered platelets and that of radiolabeled fibrinogen by thrombin-induced coagulation. Gel-filtered platelets were stimulated with ristocetin (1 mg/ml) or thrombin (0.1 U/ml) for 3 min. In some tubes thrombin, 60 s after its addition, was inhibited with 3 U/ml of hirudin. Then $^{125}$I-vWf (15 µg/ml) was added and the platelets (1×10$^8$) incubated at 37° C. without stirring. To separate the platelet-free and platelet-bound activities, the platelet suspension was layered on top of a 0.3-M sucrose with 1.35% HSA, and centrifuged at 950×g for 5 min to sediment the platelets. The supernatant was collected, the tip was cut off, and both fractions were counted for their radioactivity. The binding of $^{125}$I-fibrinogen (100 µg/ml) to ADP-stimulated and collagen-stimulated (stirred) platelets was studied similarly. The data were subjected to Scatchard analysis.

Example 10 vWf Binding to Collagen and Heparin Proteoglycans (HEP-PG)

The effects of HEP-PG, HMWH, and LMWH on vWf binding to collagen were assessed according to Lawrie et al. (Lawrie A S, Harrison P, Armstrong A L, Wilbourn B R, Dalton R G, Savidge G F., Br J Haematol 1989; 73: 100-104). For this purpose 96-well microtiter wells (Maxisorb, NUNC) were coated for 2 h at 37° C. with pepsinized type I collagen (dialyzed against 67 mM phosphate, pH 7.2) (at 50 µg/ml), then washed, and blocked with 3% BSA. vWf (0.1 µg/ml) was then added to the plates and incubated for 2 h in the presence of different concentrations of HEP-PG, HMWH and LMWH. Subsequently, bound vWf was quantified using peroxidase-conjugated polyclonal anti-vWf antibody (Dako A/S). In addition, vWf (1 µg) was incubated with HEP-PG (0.5 µg) for 10 min at 22° C. and applied to a cellulose acetate plate (Helena Lab, Tx.). The plate was electrophoresed for 30 min at 180 V in 5 mM HEPES, pH 7.4, containing 2 mM Ca$^{2+}$ and 2 mM Mg$^{2+}$, and stained with Alcian Blue to visualize HEP-PG or Ponceau red to visualize vWf.

Example 11

Statistical Analysis

Results are given as mean±SD. The statistical significance of the difference between sets of values was determined by Student's t-test for paired values or factorial ANOVA, as indicated.

Example 12

Anastomosis and Two Thrombosis Models of Microsurgery in the Rat Femoral Artery.

All procedures performed in this study were approved by the appropriate institutional guidelines and followed the administrative guidelines for animal research. Before the procedure the rats were anesthetized (Hypnorm™ 10 ml, Dormicum™ 3 ml, aqua ad 10 ml, i.p). When performing the anastomosis the femoral artery was exposed, two clamps were set, the vessel was cut, and then flushed with 100 µl of either saline, standard heparin (MW 15 kd, 1 mg/ml, 100 ATU/ml) or HEP-PG (10 µg/ml). After the procedure (about 15 min) the vessel was closed by a suture using 8-10 stiches with 10-0 microsurgical thread. Circulation was returned for 10 min, and the experiment was stopped after this by giving an overdose anethesia to the rat. Each treatment mode was tested in 5 rats.

The anastomosis site was excised for scanning electron microscopic evaluation, which was performed without knowing the treatment. Two different magnifications 75 and 500 were taken from each sample. The micrographs were analyzed by a grading system: 0-3.

In the first thrombosis model (Davidsson S F et al. Plast Rec Surg 86:579-582, 1990) the vessel was crushed for 2 min with a bulldog clamp, then the vessel was partly opened, the inner wall was scratched with a needle for 10 times, then the flushing with either saline, heparin or HEP-PG was performed, and the vessel was closed. Circulation was returned for 10 min. The rest of the experiment followed the design provided in the anastomosis model.

In the other thrombosis model (Andersen D M et al. Microsurgery 15: 413-420, 1994) the vessel was treated as in the anatomosis model but when closing the suture, the vessel was inverted into the blood stream so that all layers of the vessel, adventitia, media and intima were exposed to flowing blood. The rest of the experiment followed the design provided in the anastomosis model.

EXAMPLES SHOWING THE RESULTS

Example 13

Inhibition of Thrombin

Figure 1:
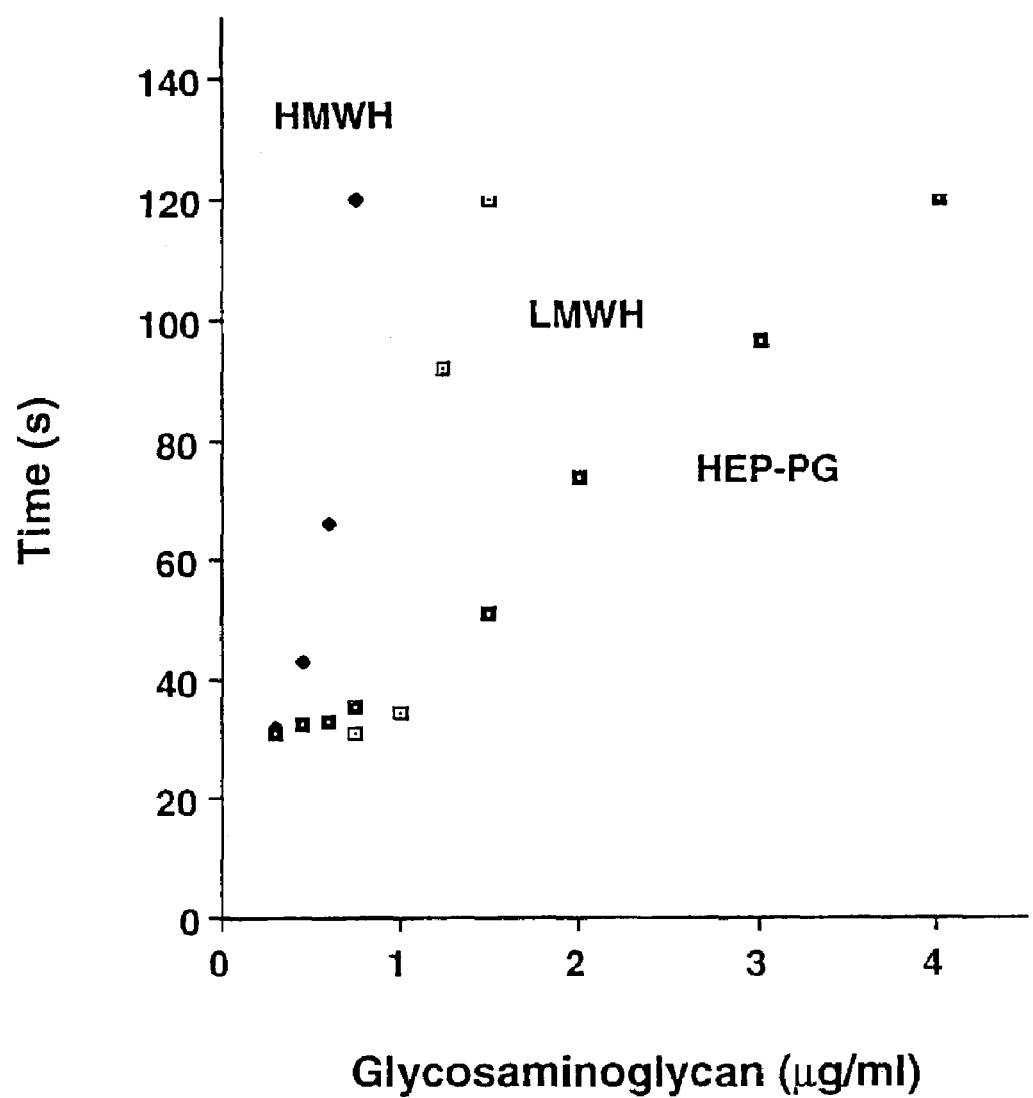
FIG. 1 shows the dose-dependent effects of the various heparin glycosaminoglycans HEP-GAG on thrombin time in citrated plasma (dilution 1:3). HMWH=high-molecular-weight or unfractionated heparin, LMWH=low-molecular-weight, or fractionated heparin, HEP-PG=mast cell-derived water soluble heparin proteoglycans.

Mast cell-derived soluble HEP-PG at concentrations exceeding 1.0 µg/ml significantly prolonged thrombin time when studied in 1:3 plasma dilution (FIG. 1). However, HEP-PG inhibited thrombin significantly less effectively than HMWH or LMWH. Also, as measured by the chromogenic assay, HEP-PG were less effective than HMWH in inhibiting thrombin in the presence of 1:5 plasma dilution. This difference could be observed at the various thrombin concentrations used (0.5-3 U/ml) (data not shown).

To study whether plasma proteins affected the ability of HEP-PG to potentiate exogenous antithrombin III or heparin cofactor 11, the effects of various concentrations of HEP-PG and HMWH on residual thrombin activity were measured in the presence and absence of plasma. At a plasma dilution (1:40), HEP-PG did not differ from HMWH (FIG. 2). In the absence of plasma, however, HEP-PG were more potent than HMWH in enhancing antithrombin III activity. Thus, HEP-PG were able to potentiate antithrombin III, but this ability was impaired in the presence of plasma proteins.

Example 14

Platelet Aggregation and Serotonin Release in Platelet-rich Plasma

Mast cell-derived HEP-PG strongly inhibited collagen-induced platelet aggregation in both types of PRP investigated. When studied in citrate-anticoagulated PRP, HEP-PG were inhibitory at a concentration of as low as 1.0 µg/ml (FIG. 2). At this concentration, HMWH and LMWH did not impair aggregation, and these heparins were without effect even if 300-fold excess (300 µg/ml) was used. We next treated the HEP-PG with alkali to dissolve their protein components and to obtain isolated glycosaminoglycan chains. The inhibitory action of the glycosaminoglycan chains, average MW 75 kDa HEP-GAG was significantly weaker than that of the native HEP-PG but significantly better than that of HMWH and LMWH. In contrast to HEP-PG, HMWH impaired collagen-induced aggregation only in citrated PRP and at low collagen concentrations (<2.0 µg/ml).

The dose-dependent effects of HEP-PG on collagen-induced aggregation in citrated and in PPACK-anticoagulated PRP showed that the inhibitory effect of HEP-PG was independent of collagen concentration up to 150 µg/ml, and more pronounced in cation-depleted plasma than in PPACK-PRP, in which total inhibition was reached only at 3 µg/ml. Inhibition was total, irrespective of whether HEP-PG and collagen were added simultaneously, or HEP-PG were added 10 s after collagen. HEP-PG also reduced the release of platelet serotonin from 50% to the background level (10%) in PRP, even at the highest collagen concentration tested (150 µg/ml).

In additional experiments we treated HEP-PG with heparinase or chondroitinase ABC. We found that treatment with heparinase totally abolished the ability of HEP-PG to inhibit collagen-induced platelet aggregation, whereas treatment of HEP-PG with chondroitinase ABC did not lessen their inhibitory potential (not shown). The macroaggregated HEP-PG complexes forming the granule remnants (i.e., the residues left over after release of the soluble proteoglycans from the exocytosed granules (Kovanen P T. Eur Heart J 14 (suppl K) 1992;105-117; Lindstedt K, Kokkonen J O, Kovanen P T. J Lipid Res 1992;33:65-74) had no inhibitory effect on collagen-induced platelet aggregation compared with the same amount of soluble HEP-PG. However, when the granule remnants were first disintegrated into HEP-PG monomers by treatment with 2 M NaCl and then added to the platelets, the inhibitory effect equaled that observed with soluble HEP-PG.

The concentration of HEP-PG, which completely abolished the collagen-induced responses of platelets (3 µg/ml; FIG. 3) was selected for testing the effects of HEP-PG on platelet aggregation induced with agonists other than collagen. As shown in Table I, HEP-PG inhibited platelet aggregation induced with ristocetin, inhibition being total at a ristocetin concentration of 0.60 mg/ml. Inhibition was also considerable at the two higher ristocetin concentrations, 0.75 and 1.0 mg/ml. HMWH and LMWH did not inhibit ristocetin-induced aggregation to the same extent as did HEP-PG. Furthermore, HEP-PG did not markedly modify platelet aggregation in response to ADP or epinephrine (10 µM) (not shown).

Example 15

Aggregation of Gel-filtered Platelets

When HEP-PG were added to suspensions of gel-filtered platelets, the collagen-induced platelet aggregation was only incompletely abolished. With 25 µg/ml of collagen the inhibitory effect of 3 µg/ml of HEP-PG ranged between 25 and 60%. We also studied thrombin-induced (0.1 and 0.25 lU/ml) aggregation of gel-filtered platelets. Again, platelet aggregation was more effectively inhibited by HEP-PG than by HMWH or LMWH (all at 3.0 µg/ml) (not shown). HMWH, if used at a 100-fold concentration (300 µg/ml), led to full inhibition at the two thrombin concentrations used.

Example 16

Interactions Between Platelets and Collagen in $Mg^{2+}$-Containing Buffer and in PRP In the following, we assessed the interaction of platelets with immobilized collagen. When $100 \times 10^6$ /ml platelets were studied at 22° C. under static, $Mg^{2+}$-dependent conditions, HEP-PG (3 µg/ml) did not affect the formation of a monolayer of adherent platelets (FIG. 3). In contrast, HEP-PG significantly inhibited the subsequent platelet-platelet interaction, when $300 \times 10^6$ /ml platelets were rotated at 37° C. In PPACK-PRP, however, HEP-PG did not significantly decrease the interaction. Under the corresponding conditions, the mAb against GP IIb/IIIa (m7E3 at 10 µg/ml) inhibited collagen-induced platelet deposition by 20%, 75%, and 80%, respectively.

Example 17A

Efficacy of Soluble HEP-PG on Interactions Between Platelets and Collagen in Flowing Blood When PPACK-anticoagulated whole blood was perfused at different shear rates through tubing coated with collagen, HEP-PG (3 µg/ml) significantly inhibited platelet deposition, but not adhesion, on the collagen. Inhibition was evident both at a low shear rate (200 1/s) and at higher shear rates (700 and 1700 1/s). When the same experiment was repeated (at 700 and 1700 1/s) using reconstituted blood without plasma, the platelets adhered to the collagen to the same extent whether HEP-PG were present or not (not shown). Scanning electron micrographs of the platelets covering the collagen-coated surface after perfusion with whole blood at 1700 1/s demonstrated complete absence of aggregates when HEP-PG were present. At this shear rate platelet adhesion was not significantly diminished in the presence of HEP-PG. Surface coverage was 22±4% in the absence and 17±5% in the presence of HEP-PG, (n=3).

Example 17B

Efficacy of Immobilized HEP-PG to Inhibit Platelet Deposition on Monomeric Collagen-coated Surface in Flowing Whole Blood The co-immobilization of collagen with HMWH and HEP-PG did not reduce collagen attachment as evidenced by Blyscan assay (North Ireland, Belfast). When 10 µg/ml of HEP-PG was immobilized on collagen type I (pepsin-treated or isolated from bovine tendon by pepsin) and it was compared with either buffer or 10 µg/ml of unfractionated heparin HMWH (molecular mass=15 kDa, Heparin, Leiras, Finland), it was found that HEP-PG reduced platelet recruitment to less than 1 tenth, whereas HMWH decreased it to one fourth. In addition to being effective in solution as shown in Example 7A, HEP-PG immobilized upon collagen surface was similarly highly effective in blocking platelet-to-platelet interaction in flowing blood. The results are shown in FIG. 6 below.

Example 17C

Efficacy of Immobilized HEP-PG to Inhibit Platelet Deposition on Fibrillar Collagen-coated Surface in Flowing Whole Blood The co-immobilization of collagen (Horm reagent) with 10 g/ml was compared with that of 10 µg/ml of unfractionated heparin. In contrast to unfractionated heparin HEP-PG significantly, by 50%, reduced platelet deposition on the surface. Thus, the efficacy of HEP-PG immobilized with monomeric collagen could also be obtained over the more native-type collagen fibers. The results are shown in FIG. 5 below.

Example 18

Binding of Fibrinogen and vWf to Platelets

HEP-PG tended to reduce the binding of fibrinogen to collagen-stimulated platelets: from 2.4±1.2 to 1.5±0.7 pmol/$10^8$ platelets (n=4, p=0.06), the background being 0.8±0.4 pmol/$10^8$ platelets, but did not affect ADP-induced binding (not shown). However, HEP-PG (3 µg/ml) inhibited vWf binding to thrombin-stimulated platelets by 40% (234 vs. 349 ng/$10^8$ platelets (Table II). HWMH at the same concentration was without significant effect, but at 100-fold excess (300 µg/ml) completely blocked vWf binding to platelets. HEP-PG did not inhibit vWf binding to ristocetin-stimulated platelets. A similar result was obtained with HMWH. Again, 100-fold excess (300 µg/ml) of HWMH significantly inhibited vWf binding to ristocetin-stimulated platelets.

Example 19

Interaction Between Platelets and Heparin Proteoglycans (HEP-PG)

When HEP-PG were immobilized instead of collagen, and platelets in PPACK-PRP were allowed to attach, the level of platelet deposition was $0.36\pm0.17\times10^6$ platelets/cm$^2$ (n=4), which did not differ from the value obtained with immobilized albumin, HSA ($0.50\pm0.31\times10^6$ platelets/cm$^2$) (n=4). The finding that platelets did not bind to HEP-PG was confirmed by experiments in which $^{35}$S-labeled HEP-PG (3-10 µg/ml) were incubated in PRP, and after the incubation the platelets were sedimented and counted for their $^{35}$S-scintillation activity. No $^{35}$S-scintillation activity was present in the sediments, indicating that HEP-PG did not cosediment with the platelets. Furthermore, when washed platelets were incubated with $^{35}$S-HEP-PG and subsequently subjected to gel filtration, $^{35}$S-HEP-PG was eluted separately after the platelet population.

Example 20 vWf Binding to Heparin Proteoglycans (HEP-PG) and to Collagen vWf and HEP-PG were electrophoresed either alone or together on a cellulose acetate plate, and the plates were stained for both protein and glycosaminoglycans to visualize the individual components. The addition of vWf to HEP-PG reversed their mobility from anodic to cathodic, implying an association between vWf and HEP-PG. Since HEP-PG had inhibited platelet-collagen interaction at a high shear rate and also interfered with the other vWf-mediated platelet functions (Table I), we studied whether HEP-PG affected vWf binding to collagen, using ELISA assay. vWf binding to collagen was not inhibited, but, on the contrary, was markedly enhanced. This result differed completely from those obtained with HMWH and LMWH. Even at a 10-fold excess concentration (30 µg/ml), as compared with HEP-PG, HMWH only slightly increased the binding of vWf to collagen, and LMWH was without any effect.

Example 21

Interaction Between Heparin Proteoglycans (HEP-PG) and Collagen

We also tested the binding of HEP-PG to collagen under conditions mimicking those in which HEP-PG inhibited the platelet-collagen interaction (i.e., at similar concentrations of HEP-PG and collagen and a similar incubation time). When collagen (whether pepsinized or fibrillar) was immobilized, it did not interact with HEP-PG. These results were obtained using $^{35}$S-HEP-PG or detecting glycosaminoglycans with Alcian Blue. Furthermore, after incubation of collagen with HEP-PG, the pellet obtained by centrifugation through a sucrose cushion failed to show Alcian Blue-reactivity.

Example 22

Collagen Induced Platelet Aggregation in the Presence of Unfractionated Heparin Cross-linked with Bovine Serum Albumin (BSA)

Figure 10:
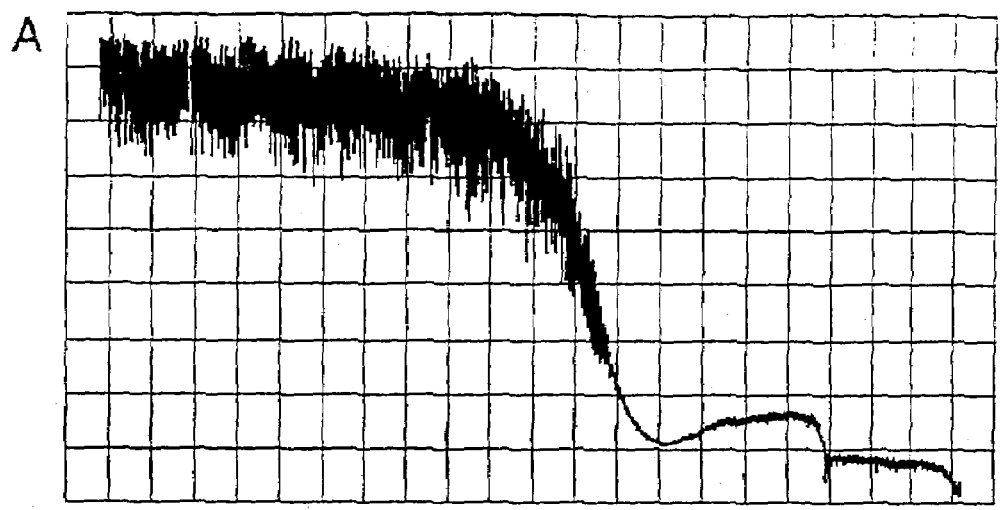
Figure 10:
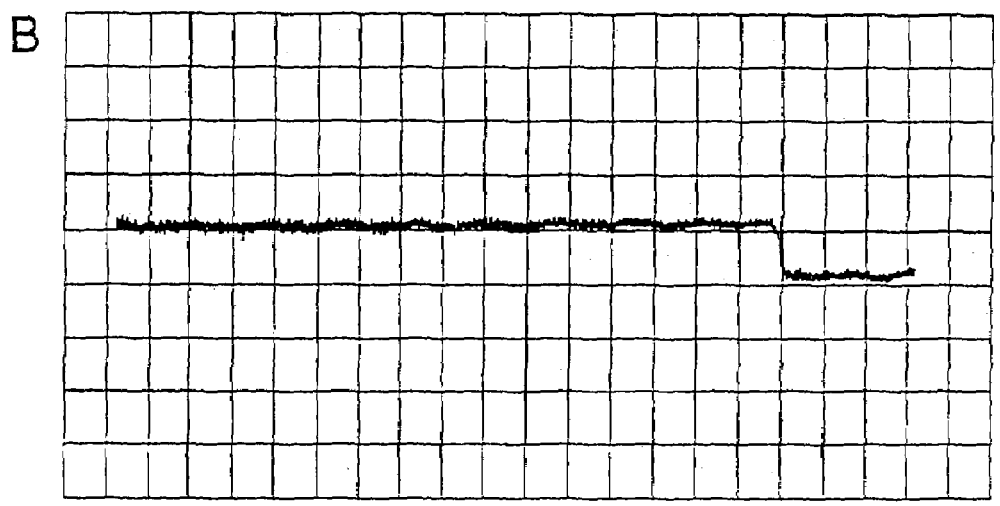
Figure 10:
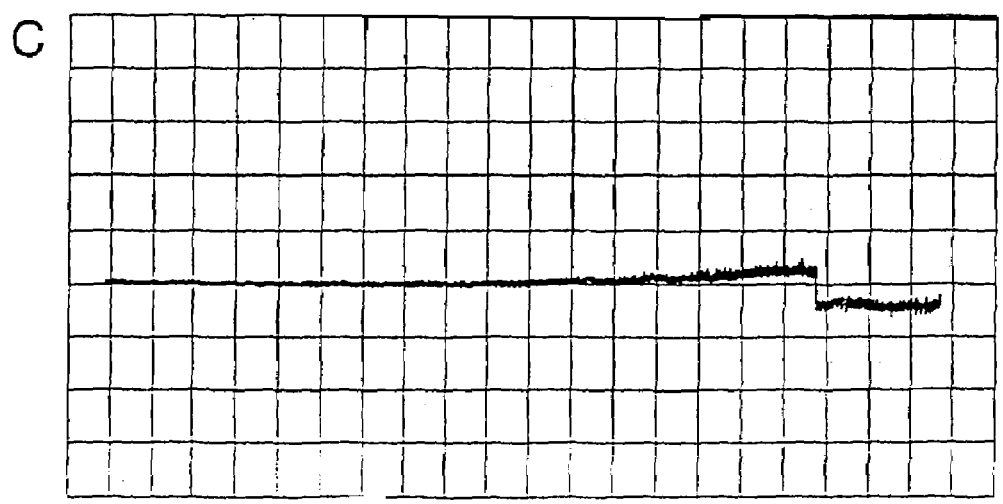

Fractions of the unfractionated heparin (12 kDa) cross-linked to bovine serum albumin as described in Example 1E were analyzed in aggregometer (see FIG. 10). As an example the aggregation curve for PD-10 separated fraction #21 having 0.74 µg/ml heparin is given. All fractions 18-21 showed inhibitory capacity against collagen-induced platelet aggregation. Hence, FIG. 10A illustrates platelet aggregation in citrated PRP preincubated with a buffer 30 µl. The response depicted is to collagen (Sigma aggregation kit collagen) 30 µl at a final concentration 25 µg/ml. In FIG. 10B PRP was preincubated for 1 min with 30 µl of HEP-PG at the final concentration of 3 µg/ml. No response to collagen (25 mg/ml) was obtained. In FIG. 10C PRP was preincubated for 1 min with 30 µl of fraction #21 albumin-coupled heparin at a concentration of 0.74 µg/ml (Blyscan). No response to collagen (25 µg/ml) was obtained.

Example 23

Results Obtained in Vivo Arterial Thrombosis Models and Model of Microsurgical Anastomosis We have obtained in vivo data in rats where HEP-PG is applied topically during femoral artery anastomosis with or without needle-scratch injury of the surface layers of the vessel and with or without improper placement of the anastomosis to create blood contact with the deeper layers of the artery, i.e. intima, media and adventitia. These studies provide experimental models for arterial thrombosis during vascular surgery and microsurgical techniques, which are often hampered by thrombotic complications.

During macroscopic inspection thrombosis occurred in the control experiment (saline administration) in nearly all animals operated, patency being 14/22, whereas the 21/22 vessels remained patent when HEP-PG at 10 µg/ml was administered locally in a volume 100 µl for the time (about 10 min) closing the anastomosis and then allowing nonanticoagulated blood flow over the injury site for 10 min before sacrificing the rat.

We studied the anastomosis model by infusing 0.5 ml "Indium"-labeled rat platelets (at 300-500×10⁶/ml) just at the time when releasing blood flow for ten minutes. Subsequently, the rat was sacrificed, and blood and anastomosis samples were collected. Gamma-counter calculations of the specific activity of platelets in blood and at the anastomosis sites, revealed significant efficacy for HEP-PG. (111-Indium-labeled platelets: NaCl 14.2±7.2 (n=7) vs.HEP-PG 7.5±2.9, ×10⁶ mean±SD, (n=7)/anastomosis area, P=0.025, ANOVA).

In scanning electron microscopic analysis significantly less thrombotic response could be detected in the HEP-PG group in the anastomosis model without any extra provocation of thrombosis (scratching or improper anastomosis). The thrombotic response remained mural and mainly consisted of adhesive layer of platelets, and the aggregates were either sporadic or absent. (FIG. 8). The comparison of scanning electron micrographs ("blinded" analysis) gave the following scores (min 1, max 4): NaCl 3.2 (n=5), HMWH 2.8 (n=5) and HEP-PG 1.8 (n=5), p=0.03, HEP-PG vs. saline in the anastomosis model; ANOVA, repeated measures. Similar results were obtained, when analysed 72 hours after the anastomosis.

TABLE I

Effects of glycosaminoglycans on ristocetin-induced platelet aggregation in PRP (citrate).

| Ristocetin (mg/ml) | Control | | HEP-PGs (3 µg/ml) | | HMWH (3 µg/ml) | | HMWH (300 µg/ml) | | LMWH (3 µg/ml) | |
|---|---|---|---|---|---|---|---|---|---|---|
| | R | MA | R | MA | R | MA | R | MA | R | MA |
| 0.60 | 0.7 | 83 | 0 | <10 | 0.8 | 85 | 0 | <10 | 0.4 | 81 |
| 0.75 | 6.4 | 100 | 0.7 | 19 | 5.0 | 100 | 1.0 | 42 | 4.7 | 100 |
| 1.00 | 6.6 | 100 | 2.7 | 59 | 5.7 | 100 | 0.5 | 52 | 6.5 | 100 |

R = rate of primary aggregation (1/min);
MA = maximal aggregation (%).
A representative platelet aggregation performed on PRP of four donors.

TABLE II

Effects of HEP-PG and HMWH on binding of vWf (final concentration 5 µg/ml) to stimulated platelets.

| | vWf bound (ng/10⁸ platelets) | | | |
|---|---|---|---|---|
| Agonist | Control | HER-PG (3 µg/ml) | HMWH (3 µg/ml) | HMWH (300 µg/ml) |
| No agonist | 125 ± 8 | | | |
| Thrombin + hirudin (0.5 U/ml + 3 U/ml) | 349 ± 72 | 234 ± 66 | 312 ± 95 | 108 ± 24 |
| m7E3 + thrombin hirudin (10 µg/ml + 0.5 U/ml + 3 U/ml) | 138 ± 10 | | | |
| Thrombin, no hirudin (0.5 U/ml) | 858 ± 36 | 808 ± 18 | — | 188 ± 40 |
| Ristocetin (1 mg/ml) | 868 ± 77 | 960 ± 202 | 746 ± 174 | 280 ± 77 |

Values are mean±SD (n=4, in duplicate).

Factorial ANOVA: Thrombin+hirudin: HEP-PG vs control, and HEP-PG vs HMWH (300 µg/ml) p<0.05; HMWH (300 µg/ml) vs control, and HMWH (300 µg/ml) vs. HMWH (3 µg/ml) p<0.001. m7E3+thrombin+hirudin: m7E3 vs control, p<0.001. Thrombin, no hirudin: HMWH (300 µg/ml) vs control and vs HEP-PG, both p<0.001. Ristocetin: HMWH (300 µg/ml) vs control, vs HEP-PG, and vs HMWH (3 µg/ml), each p<0.001,—not performed.

The invention claimed is:

1. A method for inhibiting collagen induced platelet aggregation associated with vascular or microvascular injuries and/or interventions, comprising local administration of isolated mast cell derived heparin proteoglycan, wherein the mast cell derived heparin proteoglycan provides inhibition of collagen-induced platelet aggregation with preserved platelet adhesion on collagen in flowing blood.

2. The method of claim 1, wherein the local administration is performed by applying an effective amount of the mast cell derived heparin proteoglycan as a preparation.

3. The method of claim 1, wherein the local administration is performed by applying an effective amount of the mast cell derived heparin proteoglycan as a device coated with a preparation comprising mast cell derived heparin proteoglycan.

* * * * *

UNITED STATES PATENT AND TRADEMARK OFFICE
CERTIFICATE OF CORRECTION

PATENT NO.       : 7,314,860 B2
APPLICATION NO.  : 10/418095
DATED            : January 1, 2008
INVENTOR(S)      : Riitta Lassila et al.

Page 1 of 1

It is certified that error appears in the above-identified patent and that said Letters Patent is hereby corrected as shown below:

Title Page, Item (73) Assignee should read:

--Jenny ja Antti Wihurin Rahasto--

Signed and Sealed this

Third Day of June, 2008

JON W. DUDAS
*Director of the United States Patent and Trademark Office*